United States Patent [19]
Maruta et al.

[11] Patent Number: 5,922,580
[45] Date of Patent: *Jul. 13, 1999

[54] NON-REDUCING SACCHARIDE-FORMING ENZYME, ITS PREPARATION AND USES

[75] Inventors: Kazuhiko Maruta, Okayama; Michio Kubota, Osaka; Toshiyuki Sugimoto; Toshio Miyake, both of Okayama, all of Japan

[73] Assignee: Kabushiki Kaisha Hayashibara Seibutsu Kagaku Kenkyujo, Okayama, Japan

[*] Notice: This patent is subject to a terminal disclaimer.

[21] Appl. No.: 08/941,553

[22] Filed: Sep. 30, 1997

Related U.S. Application Data

[60] Continuation of application No. 08/487,396, Jun. 7, 1995, Pat. No. 5,716,838, which is a division of application No. 08/172,707, Dec. 27, 1993, Pat. No. 5,455,168.

[30] Foreign Application Priority Data

Dec. 28, 1992 [JP] Japan ................................. 4-362131
Sep. 30, 1993 [JP] Japan ................................. 5-265416

[51] Int. Cl.[6] ........................... C12P 19/12; C12N 1/20; C07H 3/02; C07H 3/06
[52] U.S. Cl. ........................ 435/100; 435/101; 435/99; 435/253.1; 435/252.1; 514/53; 514/54; 514/60; 426/658; 536/123.13; 536/123.12; 536/123.1; 536/126
[58] Field of Search ..................... 536/123.13, 123.12, 536/123.1, 126; 514/53, 54, 60; 426/658; 435/100, 101, 99, 253.1, 252.1

[56] References Cited

U.S. PATENT DOCUMENTS

| | | | |
|---|---|---|---|
| 4,521,252 | 6/1985 | Miyake et al. | |
| 5,472,863 | 12/1995 | Maruta et al. | 435/200 |
| 5,714,368 | 2/1998 | Nakada et al. | 435/201 |

FOREIGN PATENT DOCUMENTS

| | | |
|---|---|---|
| 0447125 | 9/1991 | European Pat. Off. |
| 0555540 | 8/1993 | European Pat. Off. |
| 0609801 | 8/1994 | European Pat. Off. |
| 0619951 | 10/1994 | European Pat. Off. |
| 2671099 | 7/1992 | France |
| 50154485 | 12/1975 | Japan |
| 5872598 | 2/1983 | Japan |
| 5823799 | 4/1983 | Japan |
| 58216695 | 12/1983 | Japan |
| 4281795 | 9/1991 | Japan |
| 2106912 | 3/1986 | United Kingdom |
| WO-A-92 03565 | 3/1992 | WIPO |

OTHER PUBLICATIONS

"Biseibutsu–no–Bunrui–to–Dotei", (Classification and Identification of Microorganisms), edited by T. Hasegawa, Japan Scientific Societies Press, Tokyo, Japan (1985).
"Current Status of Starch Application Development and Related Problems," *Food Chemicals*, No. 88, pp. 67–72, Aug. 1992.
Database WPI, Section Ch, Week 9425, Derwent Publications Ltd., London, GB; Class D16, An 94–206435; "Alpha, Alpha–Trehalose Production Comprising Extraction from Yeast and Water, and Treatment with Ultrafiltration or Reverse Osmosis"; and JP, A, 06 145 186 (Kirin Brewery KK and Nippon Shokuhin Kako KK), May 24,1994, Abstract.
Hoelzle et al., "Increased Accumulation of Trehalose in Rhizobia Cultured Under 1% Oxygen", *Applied and Environmental Microbiology*, pp. 3213–3215, Oct. 1990.
*Handbook of Amylases and Related Enymes*, The Amylase Research Society of Japan, Pergamon Press, 1988.
*Bergey's Manual of Systematic Bacteriology*, vol. 1, William & Wilkins, 1984.
*Bergey's Manual of Systematic Bacteriology*, vol. 2, William & Wilkins, 1986.
*Advances in Carbohydrate Chemistry*, Academic Press, 1963.
*Journal of Clinical Nutrition*, vol. 41, No. 2, pp. 200–208, (1972).
Journal Of The Chemical Society, May 1965 Letchworth, G.B., pp. 3489–3490, Birch, "A Method of Obtaining Crystalline Anhydrous Alpha–Alpha Trehalose". Biotechnology Letters, vol. 12, No. 6, Jun. 1990, pp. 431–432, LAMA et al., "Starch Conversion With Immobilized Thermophilic Archebacterium *Sulfoldous Solfatarious*".
ATCC Catalogue of Bacteria and Bacteriophages, 17 Ed., 1989, pp. 46, 131 and 141.

*Primary Examiner*—Francisco Prats
*Attorney, Agent, or Firm*—Browdy & Neimark

[57] ABSTRACT

Disclosed are novel non-reducing saccharide-forming enzyme, and its preparation and uses. The enzyme is obtainable from the culture of microorganisms such as Rhizobium sp. M-11 (FERM BP 4130) and Arthrobacter sp. Q36 (FERM BP-4316), and capable of forming non-reducing saccharides having a trehalose structure when allowed to act on reducing partial starch hydrolysates. Glucoamylase and α-glucosidase readily yield trehalose when allowed to act on the non-reducing saccharides. These non-reducing saccharides and trehalose are extensively useful in food products, cosmetics and pharmaceuticals.

13 Claims, 8 Drawing Sheets

5,922,580

```
                           SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1
             (D) OTHER INFORMATION: /note= "Xaa = valine or methionine"

(xi) SEQUENCE DESCRIPTION: SEQ ID NO:1:

Xaa Arg Thr Pro Ala Ser Thr Tyr Arg Leu
   1               5                   10

(2) INFORMATION FOR SEQ ID NO:2:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:2:

Met Arg Thr Pro Val Ser Thr Tyr Arg Leu
   1               5                   10

(2) INFORMATION FOR SEQ ID NO:3:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:3:

Gly Val Glu Asp Thr Ala Phe Phe Arg Tyr
   1               5                   10

(2) INFORMATION FOR SEQ ID NO:4:

(i) SEQUENCE CHARACTERISTICS:
             (A) LENGTH: 10 amino acids
             (B) TYPE: amino acid
             (C) STRANDEDNESS: single
             (D) TOPOLOGY: linear
```

(ii) MOLECULE TYPE: peptide (xi) SEQUENCE DESCRIPTION: SEQ ID NO:4:

Leu Val Gln Leu Thr Met Pro Gly Val Pro
1               5                   10

(2) INFORMATION FOR SEQ ID NO:5:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Glu Gly Arg Gly Ser Pro Tyr Ala Val Ala
1               5                   10

(2) INFORMATION FOR SEQ ID NO:6:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Gly Val Glu Asp Thr Ala Phe Phe Arg Tyr
1               5                   10

(2) INFORMATION FOR SEQ ID NO:7:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Leu Val Gln Leu Thr Met Pro Gly Val Pro
1               5                   10

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Glu Gly Arg Gln Ser Arg Tyr Ala Glu Ala
1               5                   10

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Xaa = valine or methionine"

(ix) FEATURE:
            (A) NAME/KEY: Peptide
            (B) LOCATION: 5
            (D) OTHER INFORMATION: /note= "Xaa = alanine or valine"

(xi) SEQUENCE DESCRIPTION: SEQ ID NO:9:

Xaa Arg Thr Pro Xaa Ser Thr Tyr Arg Leu
1               5                   10

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 4
            (D) OTHER INFORMATION: /note= "Xaa = glycine or glutamine"

(ix) FEATURE:
            (A) NAME/KEY: Peptide
            (B) LOCATION: 6
            (D) OTHER INFORMATION: /note= "Xaa = proline or arginine"

(ix) FEATURE:
            (A) NAME/KEY: Peptide
            (B) LOCATION: 9
            (D) OTHER INFORMATION: /note= "Xaa = valine or glutamic acid"

(xi) SEQUENCE DESCRIPTION: SEQ ID NO:10:

Glu Gly Arg Xaa Ser Xaa Tyr Ala Xaa Ala
1               5                   10

NON-REDUCING SACCHARIDE-FORMING ENZYME, ITS PREPARATION AND USES

This is a continuation of parent application Ser. No. 08/487,396 filed Jun. 7, 1995 now U.S. Pat. No. 5,716,838, itself a divisional application of Ser. No. 08/172,707 filed Dec. 27, 1993, now U.S. Pat. No. 5,455,168 granted on Oct. 3, 1995.

BACKGROUND OF THE INVENTION

1. Field of the Invention

The present invention relates to a novel non-reducing saccharide-forming enzyme, and its preparation and uses, more particularly, to a novel non-reducing saccharide-forming enzyme which forms a non-reducing saccharide having a trehalose structure when allowed to act on one or more reducing partial starch hydrolysates having a degree of glucose polymerization of 3 or higher, as well as to its preparation and microorganisms capable of producing said enzyme. The present invention further relates to a composition containing a non-reducing saccharide having a trehalose structure as an end unit which is preparable with said enzyme, a relatively-low reducing saccharide containing said non-reducing saccharide, and/or trehalose prepared from these saccharides.

2. Description of the Prior Art

Trehalose or α, α-trehalose has long been known as a non-reducing saccharide consisting of glucose units. As described in *Advances in Carbohydrate Chemistry*, Vol.18, pp.201–225 (1963), published by Academic Press, USA, and *Applied and Environmental Microbiology*, Vol.56, pp.3, 213–3,215 (1990), trehalose widely exists in microorganisms, mushrooms, insects, etc., though the content is relatively low. Since non-reducing saccharides including trehalose do not react with substances containing amino groups such as amino acids and proteins, they neither induce the amino-carbonyl reaction nor alter amino acid-containing substances. Thus, non-reducing saccharides can be used with amino acids without causing browning and deterioration. Because of this, there has been in great demand to establish a method for preparation of such a non-reducing saccharide.

In conventional preparations of trehalose, as disclosed in Japanese Patent Laid-Open No.154,485/75, microorganisms are utilized, or as proposed in Japanese Patent Laid-Open No.216,695/83, maltose is converted into trehalose by using maltose- and trehalose-phosphorylases in combination. The former, however, is not suitable for industrial-scale preparation because the content of trehalose present in microorganisms as a starting material is usually lower than 15 w/w % (the wording "w/w %" will be abbreviated as "%" in the specification, if specified otherwise), on a dry solid basis (d.s.b.), and the extraction and purification steps are complicated. The latter has the following demerits: (i) Since trehalose is formed via glucose-1-phosphate, maltose as a substrate could not be used at a relatively-high concentration; (ii) Since the enzymatic reaction systems of the phosphorylases are reversible reactions, the yield of the objective trehalose is relatively low; and (iii) it is substantially difficult to maintain the reaction systems stably and to continue their enzymatic reactions smoothly. Thus, there has not yet been realized as an industrial-scale preparation of trehalose.

As regards the preparation of trehalose, it is reported in the column titled "Oligosaccharides" in the chapter titled "Current Status of Starch Application Development and Related Problems" in *"Food Chemicals"*, No.88, pp.67–72 (August, 1992) that "In spite of a wide applicability of trehalose, an enzymatic preparation thereof via a direct saccharide-transfer reaction or a hydrolytic reaction has been reported to be scientifically almost impossible in this field." Thus, an enzymatic preparation of trehalose by using starch as a material has been deemed to be scientifically very difficult.

It is known that partial starch hydrolysates, prepared from material such as liquefied starch, cyclodextrins and maltooligosaccharides, usually have a reducing end-group as an end unit. These partial starch hydrolysates are referred to as "non-reducing partial starch hydrolysates" in the specification. The reducing power of such reducing partial starch hydrolysates is generally expressed by "Dextrose Equivalent (DE) value", based on their content of dry solid. It is known that among reducing partial starch hydrolysates those with a relatively-high DE value generally have a decreased molecular weight and viscosity and an increased sweetness and reactivity, and readily react with substances having amino groups such as amino acids and proteins to cause an undesirable browning, smell and deterioration of their quality.

These unfavorable properties of reducing partial starch hydrolysates are related to their DE values, and the relationship between reducing partial starch hydrolysates and their DE values is very important. It has been even believed to be impossible to interfere with the relationship in this field.

The only way to eliminate the relationship is a by forming non-reducing saccharides from reducing partial starch hydrolysates by hydrogenating the hydrolysates at a relatively-high pressure of hydrogen to convert their reducing end-groups into hydroxyl groups. The method, however, requires a high-pressure autoclave and consumes large amounts of hydrogen and energy, and requires a relatively-high level of control or safety precautions to prevent disasters. The material reducing partial starch hydrolysates and the resultant products differ because the former consists of glucose units and the latter, i.e. sugar alcohols of the resultant partial starch hydrolysates, consists of glucose and sorbitol units which may cause symptoms such as digestive disorder and diarrhea when ingested. Thus, there has been a great demand for decreasing or even eliminating the reducing power of reducing partial starch hydrolysates without changing glucose units as a constituent saccharide thereof.

SUMMARY OF THE INVENTION

The present invention provides a novel non-reducing saccharide, and its uses and preparations from reducing partial starch hydrolysates in order to eliminate a conventionally believed relationship between reducing partial starch hydrolysates and their DE values, as well as to explore a novel applicability of such a non-reducing saccharide.

In order to attain the aforementioned object, the present inventors have extensively screened microorganisms capable of producing a novel non-reducing saccharide-forming enzyme, which forms non-reducing saccharides having a trehalose structure when allowed to act on reducing partial starch hydrolysates.

As a result, we isolated novel microorganisms of the genera Rhizoblum, named as "Rhizobium sp. M-11", and Arthrobacter, named as "Arthrobacter sp. Q36", from the respective soils in Okayama-city, Okayama, Japan, and in Soja-city, Okayama, Japan; and found that the microorganisms produce a novel non-reducing saccharide-forming enzyme which forms non-reducing saccharides having a trehalose structure when allowed to act on reducing partial starch hydrolysates, and that the objective non-reducing saccharides are readily prepared when the enzyme is allowed to act on reducing partial starch hydrolysates.

We also found that trehalose can be prepared by first allowing the enzyme to act on reducing partial starch hydrolysates, then subjecting the resultant non-reducing saccharides to the action of glucoamylase or α-glucosidase. Thus, the present inventors accomplished this invention. Also, we extensively screened microorganisms capable of producing the enzyme from conventional microorganisms.

As a result, it was found that microorganisms of the genera Brevibacterium, Flavobacterium, Micrococcus, Curtobacterium and Terrabacter produce the present non-reducing saccharide-forming enzyme as the microorganisms of the genera Rhizobium and Arthrobacter, and we accomplished this invention. Also, we established preparations of compositions such as food products, cosmetics and pharmaceuticals which contain the present non-reducing saccharides, relatively-low reducing saccharides containing the non-reducing saccharides and/or trehalose prepared from these saccharides, and accomplished this invention.

BRIEF EXPLANATION OF THE ACCOMPANYING DRAWINGS

DETAILED DESCRIPTION OF THE INVENTION

Figure 1:
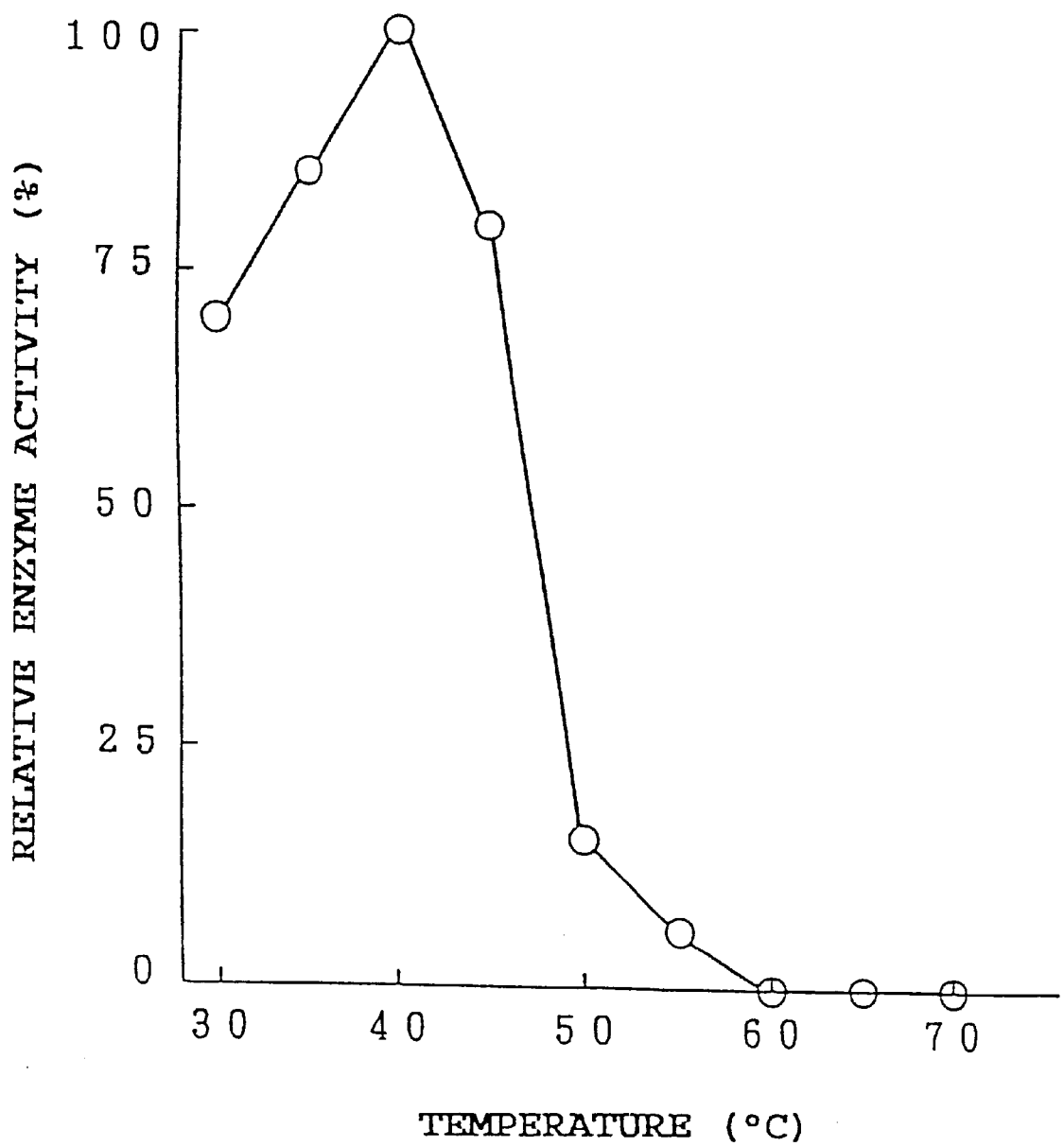
FIG. 1 shows the influence of temperature on the activity of non-reducing saccharide-forming enzyme derived from Rhizobium sp. M-11.

The present invention relates to a novel non-reducing saccharide-forming enzyme, and its preparation and uses. The present invention further relates to a microorganism capable of producing said enzyme, non-reducing saccharides prepared with said enzyme, relatively-low reducing saccharides containing said non-reducing saccharides, trehalose prepared from these saccharides, and compositions containing either or both of these saccharides and trehalose.

The present inventors have extensively screened microorganisms capable of producing a novel non-reducing saccharide-forming enzyme which forms non-reducing saccharides having a trehalose structure when allowed to act on reducing partial starch hydrolysates, and eventually found the objective microorganisms.

Now, the present inventors first explain the identification test of the microorganism of the genus Rhizobium, i.e. "Rhizobium sp. M-11" according to the present invention. The test was conducted in accordance with the method as described in "*Biseibutsu-no-Bunrui-to-Dotei*" (Classification and Identification of Microorganisms), edited by Takeji Hasegawa, published by Japan Scientific Societies Press, Tokyo, Japan (1985). The results were as follows:

A. Morphology
  Characteristics of cells when incubated at 27° C. in nutrient agar
  Usually existing in a rod form of 0.6–0.8×1.0–1.5 μm;
  Existing single but infrequently uncommonly existing in a coupled- or linked-form;
  Exhibiting no polymorphism;
  Possessing motility, asporogenicity and flagellum;
  Non-acid fast;
  Gram stain: Negative;
  Capsule: Negative;
  Metachromatic granule: Positive; and
  Accumulating poly-β-hydroxy butyrate.

B. Cultural property
  (1) Characteristics of colony formed when incubated at 27° C. in nutrient agar plate
    Shape: Circular colony having a diameter of about 1.5 mm after 24-hours incubation;
    Rim: Entire;
    Projection: Plane or hemispherical shape;
    Gloss: Positive;
    Surface: Smooth; and
    Color: Creamy and Semitransparent;
  (2) Characteristics of colony formed when incubated at 27° C. in agar plate with dextrose and trypton
    Creamy and semitransparent colony with mucoid;
  (3) Characteristics of colony formed when incubated at 27° C. in agar plate with yeast extract and mannitol
    Shape: Circular colony having a diameter of about 3 mm after 5-days incubation; and
    Color: Creamy and semitransparent colony with mucoid;
  (4) Characteristics of colony formed when incubated at 27° C. in agar plate with yeast extract, mannitol and congo red;
    Exhibiting a pale pink and substantially a no absorption of congo red;
  (5) Growing at 27° C. in agar plate with yeast extract, mannitol and 2 w/v % NaCl;
  (6) Characteristics of colony formed when incubated at 27° C. in slant nutrient agar
    Growth: Satisfactory;
    Shape: Thread-like; and
  (7) Not liquefying gelatin when stab-cultured at 27° C. in nutrient gelatin.

C. Physiological properties
  (1) Reduction of nitrate: Positive
  (2) Denitrification reaction: Negative
  (3) Methyl red test: Negative
  (4) VP-test: Negative
  (5) Formation of indole: Negative
  (6) Formation of hydrogen sulfide: Positive
  (7) Hydrolysis of starch: Negative
  (8) Utilization of citric acid: Positive
  (9) Utilization of inorganic nitrogen source: Utilizing ammonium salts and nitrates;
  (10) Formation of pigment: Forming no soluble pigment;
  (11) Urease: Positive

(12) Oxidase: Negative
(13) Catalase: Positive
(14) Growth conditions: Growing at a pH in the range of 5.5–9.0 and a temperature in the range of 4–35° C.;
(15) Oxygen requirements: Aerobic
(16) Utilization of carbon source and acid formation

| Carbon source | Utilization | Acid formation |
|---|---|---|
| D-Glucose | + | + |
| D-Galactose | + | + |
| D-Fructose | + | + |
| L-Arabinose | + | + |
| D-Xylose | + | + |
| L-Rhamnose | + | + |
| Maltose | + | − |
| Sucrose | + | + |
| Lactose | + | − |
| Trehalose | + | − |
| Raffinose | + | + |
| Mannitol | + | − |
| Dextrin | + | − |
| Dulcitol | + | − |

(17) Decarboxylase test on amino acid
  Negative against L-lysine, L-arginine and L-ornithine;
(18) Utilization of amino acid
  Utilizing sodium L-glutamate, sodium L-asparate, L-histidine and L-proline;
(19) DNase: Negative;
(20) Formation of 3-ketolactose: Negative; and
(21) Mol % guanine (G) plus cytosine (C) of DNA: 61%.

The bacteriological properties were compared with those of known microorganisms with reference to *Bergey's Manual of Systematic Bacteriology*, Vol.1 (1984). As a result, it was revealed that the microorganism was identified as a microorganism of the genus Rhizobium. The microorganism is similar to those of the species *Rhizobium meliloti* in some properties, but they are distinguishable with the fact that the present microorganism utilizes maltose, lactose and mannitol but forms no acid, and it produces a non-reducing saccharide-forming enzyme which forms non-reducing saccharides having a trehalose structure when allowed to act on reducing partial starch hydrolysates. No publications have reported such a microorganism having these properties.

Based on these results, the present inventors named this microorganism "Rhizobium sp. M-11", and deposited it on Dec. 24, 1992, in Fermentation Research Institute, Agency of Industrial Science and Technology, Ibaraki, Japan. The deposition of the microorganism was accepted on the same day and has been maintained by the institute under the accession number of FERM BP-4130.

In addition to the above-identified microorganism, other strains of the genus Rhizobium and their mutants can be suitably used in the invention as long as they produce the present non-reducing saccharide-forming enzyme.

The identification test of a microorganism of the genus Arthrobacter, i.e. Arthrobacter sp. Q36 according to the present invention gave the following results. The test was conducted similarly as in Rhizobium sp. M-11 in accordance with the method as described in *"Biseibutsu-no-Bunrui-to-Dotei"* (Classification and Identification of Microorganisms), edited by Takeji Hasegawa, published by Japan Scientific Societies Press, Tokyo, Japan (1985). The results were as follows:

A. Morphology (1) Characteristics of cells when incubated at 27° C. in nutrient agar
  Usually exhibiting a rod form of 0.5–0.7×0.8–1.6 $\mu$m; Existing single;
  Exhibiting polymorphism;
  Possessing no motility, flagellum and asporogenicity;
  Non-acid fast;
  Gram stain: Positive;
  Capsule: Negative; and
(2) Characteristics of cells when incubated at 27° C. in EYG agar
  Exhibiting a rod-coccus cycle.

B. Cultural property
  (1) Characteristics of colony formed when incubated at 27° C. in nutrient agar plate
    Shape: Circular colony having a diameter of about 2–2.5 mm after 3-days incubation;
    Rim: Entire;
    Projection: Hemispherical shape;
    Gloss: Moist gloss;
    Surface: Smooth; and
    Color: Semitransparent and white or pale yellow;
  (2) Characteristics of cells when slant-cultured at 27° C. in nutrient agar plate
    Growth rate: Satisfactory; and
    Shape: Thread-like;
  (3) Characteristics of cells when slant-cultured at 27° C. in agar plate containing yeast extract and peptone
    Growth rate: Satisfactory; and
    Shape: Thread-like; and
  (4) Characteristics of cells when stub-cultured at 27° C. in bouillon and gelatin Liquefying bouillon and gelatin.

C. Physiological properties
  (1) Reduction of nitrate: Positive
  (2) Denitrification reaction: Negative
  (3) Methyl red test: Negative
  (4) VP-test: Positive
  (5) Formation of indole: Negative
  (6) Formation of hydrogen sulfide: Positive
  (7) Hydrolysis of starch: Negative
  (8) Hydrolysis of cellulose: Negative
  (9) Utilization of citric acid: Positive
  (10) Utilization of inorganic nitrogen source: Utilizing ammonium salts and nitrates;
  (11) Formation of pigment: Negative;
  (12) Urease: Positive;
  (13) Oxidase: Negative;
  (14) Catalase: Positive;
  (15) Growth conditions: Growing at a pH in the range of 5–10 and a temperature in the range of 4–37° C.;
  (16) oxygen requirements: Aerobic;
  (17) Utilization of carbon source and acid formation

| Carbon source | Utilization | Acid formation |
|---|---|---|
| D-Glucose | + | − |
| D-Galactose | + | − |
| D-Fructose | + | − |
| L-Arabinose | + | − |
| D-Xylose | + | − |
| L-Rhamnose | + | − |
| Maltose | + | − |
| Sucrose | + | − |
| Lactose | + | − |
| Raffinose | + | − |

-continued

| Carbon source | Utilization | Acid formation |
|---|---|---|
| Mannitol | + | − |
| Dextrin | + | − |
| Dulcitol | + | − |

(18) Utilization of amino acid
   Utilizing sodium L-glutamate, sodium L-asparate, L-histidine and L-proline;
(19) DNase: Positive;
(20) Formation of 3-ketolactose: Negative;
(21) Major diamino acid of cell wall: Lysine; and
(22) Mol % guanine (G) plus cytosine (C) of DNA: 63%.

The bacteriological properties were compared with those of known microorganisms with reference to *Bergey's Manual of Systematic Bacteriology*, Vol.2 (1984). As a result, it was revealed that the microorganism was identified as a microorganism of the genus Arthrobacter. The microorganism is characterized by producing a non-reducing saccharide-forming enzyme which forms non-reducing saccharides having a trehalose structure when allowed to act on reducing partial starch hydrolysates. No publications have reported such an enzyme.

Based on these results, the present inventors named this microorganism "Arthrobacter sp. Q36", and deposited it on Jun. 3, 1993, in National Institute of Bioscience and Human-Technology Agency of Industrial Science and Technology, Ibaraki, Japan. The deposition of the microorganism was accepted on the same day and has been maintained by the institute under the accession number of FERM BP-4316.

In addition to the above-mentioned microorganism, other strains of the genus Arthrobacter and their mutants can be suitably used in the invention as long as they produce the present non-reducing saccharide-forming enzyme when allowed to act on reducing partial starch hydrolysates.

Any microorganism can be used in the invention as long as it produces the present enzyme. For example, in addition to the aforementioned Rhizobium sp. M-11 (FERM BP-4130) and Arthrobacter sp. Q36 (FERM BP-4316), other hitherto known microorganisms such as those of the species *Brevibacterium helovolum* (ATCC 11822), *Flavobacterium aquatitle* (IFO 3772), *Micrococcus luteus* (IFO 3064), *Micrococcus roseus* (ATCC 186), *Curtobacterium citreum* (IFO 15231), *Mycobacterium smegmatis* (ATCC 19420), *Terrabacter tumescens* (IFO 12960) and their mutants can be favorably used in the invention.

Any nutrient culture medium can be used in the invention as long as these microorganisms can grow therein and produce the present non-reducing saccharide-forming enzyme: For example, synthetic- and natural-nutrient culture media can be used as the nutrient culture medium. Any carbon-containing substance can be used in the invention as a carbon source as long as it is utilized by the microorganisms: Examples of such a carbon source are saccharides such as glucose, fructose, lactose, sucrose, mannitol, sorbitol, molasses and reducing partial starch hydrolysates; and organic acids such as citric acid and succinic acid. The concentrations of these carbon sources in nutrient culture media are appropriately chosen. For example, in the case of using reducing partial starch hydrolysates, a preferable concentration is usually 20% or lower, more particularly, 5% or lower, d.s.b., in view of the growth of microorganisms. The nitrogen sources usable in the invention are, for example, inorganic nitrogen compounds such as ammonium salts and nitrates; and organic nitrogen-containing substances such as urea, corn steep liquor, casein, peptone, yeast extract and beef extract. The inorganic ingredients usable in the invention are, for example, calcium salts, magnesium salts, potassium salts, sodium salts, phosphates and other salts of manganese, zinc, iron, copper, molybdenum and cobalt. If necessary, amino acids and vitamins can be suitably used in combination.

The microorganisms usable in the invention are cultured under aerobic conditions at a temperature, usually, in the range of 4–40° C., preferably, in the range of 20–37° C.; and at a pH in the range of 4–10, preferably, a pH in the range of 5–9. The cultivation time used in the invention is set to a time longer than that required for the growth initiation of the microorganisms, preferably, 10–100 hours. The concentration of dissolved oxygen (DO) in nutrient culture media is not specifically restricted, but usually in the range of 0.5–20 ppm. The concentration of DO can be kept within the range by controlling aeration, stirring, aeration with oxygen, and increasing the inner pressure of a fermentor. The cultivation is carried out batchwise or in a continuous manner.

After completion of the cultivation of microorganisms, the present enzyme is recovered. Inasmuch as the activity of the present enzyme is found in both cells and cell-free supernatants, these cells and supernatants can be recovered as a crude enzyme. The resultant culture can be also used intact as a crude enzyme. Conventional liquid-solid separation methods can be employed in the invention to remove cells from the culture. For example, methods to directly centrifuge the resultant culture, as well as those to filtrate the culture with precoat filters or to separate cells by membrane filtration using plane filters or follow fibers, can be suitably used. While cell-free filtrates thus obtained can be used intact as an enzyme solution, they may be concentrated prior to their use. The concentration methods usable in the invention are, for example, salting out using ammonium sulfate, sedimentation using acetone and alcohol, and concentration using membranes such as plane filters and follow fibers.

Cell-free filtrates and their concentrates can be subjected to conventional immobilization. Examples of such conventional methods are conjugation methods using ion exchangers, covalent bondings and absorptions using resins and membranes, and inclusion methods using high-molecular weight substances. Cells separated from the resultant cultures can be used as a crude enzyme without any treatment, or they can be immobilized prior to their use. For example, such cells are immobilized by mixing them with sodium alginate, and dropping the resultant mixture in calcium chloride solution to gelatinize the drops into granules. The granules thus obtained can be fixed by treating them with polyethylene imine or glutaraldehyde. Extracts from cells can be used in the invention as a crude enzyme solution. For example, a clear crude enzyme solution containing the present enzyme can be prepared by extracting the present enzyme from cells treated with ultrasonic, mechanical disruption using glass beads and alumina, and french-press disruption; and subjecting the resultant extract to centrifugation or membrane filtration.

The crude enzyme solution thus obtained can be used intact or after purification with conventional methods. For example, a purified enzyme preparation exhibiting an electrophoretically single band can be prepared by dialyzing a crude enzyme preparation which had been prepared by salting out a crude enzyme solution with ammonium sulfate and concentrating the resultant; and successively purifying the dialyzed solution on anion-exchange column chromatography using "DEAE Toyopearl®", an anion-exchange resin; hydrophobic column chromatography using "Butyl Toyopearl®", a hydrophobic resin; and gel filtration chromatography using "Toyopearl® HW-55", a resin for gel filtration, all of which are products of Tosoh Corporation, Tokyo, Japan.

The present non-reducing saccharide-forming enzyme thus obtained has the following physicochemical properties:

(1) Action
  Forming non-reducing saccharides having a trehalose structure as an end unit when allowed to act on one or more reducing partial starch hydrolysates having a degree of glucose polymerization of 3 or higher;
(2) Molecular weight
  About 76,000–87,000 daltons on sodium dodecylsulfate-polyacrylamide gel electrophoresis (SDS-PAGE);
(3) Isoelectric point (pI)
  About 3.6–4.6 on isoelectrophoresis using ampholyte;
(4) Optimum temperature
  About 35–40° C. when incubated at pH 7.0 for 60 min
(5) Optimum pH
  About 6.4–7.2 when incubated at 40° C. for 60 min;
(6) Thermal stability
  Stable up to a temperature of about 35–40° C. when incubated at pH 7.0 for 60 min; and
(7) pH Stability
  Stable at a pH in the range of about 5.5–11.0 when incubated at 25° C. for 16 hours.

The activity of the present non-reducing saccharide-forming enzyme is assayed as follows: One ml of an enzyme solution is added to 4 ml of 1.25 w/v % maltopentaose in 50 mM phosphate buffer (pH 7.0), and the mixture solution is incubated at 40° C. for 60 min. The reaction mixture is heated at 100° C. for 10 min to inactivate the enzymatic reaction, and the reaction mixture is precisely diluted 10 times with deionized water, followed by determining the reducing power of the diluted solution on the Somogyi-Nelson's method. As a control, an enzyme solution, which had been heated at 100° C. for 10 min to inactivate the enzyme, is treated similarly as above. One unit activity of the present enzyme is defined as the amount of enzyme which eliminates the reducing power of that of one micromole of maltopentaose per minute.

Reducing partial starch hydrolysates, which can be used as a substrate for the present enzyme, are those prepared by partially hydrolyzing amylaceous substances such as starch, amylopectin and amylose by amylases or acids. Such reducing partial starch hydrolysates obtained by the hydrolysis with amylases include those having linear and branched chain-structures prepared by hydrolyzing amylaceous substances with amylases such as α-amylase, maltotriose forming amylase, maltotetraose forming amylase, maltopentaose forming amylase and maltohexaose forming amylase as disclosed in *Handbook of Amylases and Related Enzymes*, published by Pergamon Press, Tokyo, Japan (1988). In the case of preparing the reducing partial starch hydrolysates, debranching enzymes such as pullulanase and isoamylase can be favorably used in combination with the amylases. One or more maltooligosaccharides such as maltotriose, maltotetraose, maltopentaose, maltohexaose and maltoheptaose can be arbitrary used as a reducing partial starch hydrolysate.

The concentration of the reducing partial starch hydrolysates used as a substrate in the invention is not specifically restricted. While the present enzymatic reaction proceeds even with a 0.1% solution of a substrate, the enzymatic reaction more favorably proceeds with solutions having a concentration of 2% or higher, preferably, those having a concentration of 5–50% of a substrate, d.s.b. Under these concentrations non-reducing saccharides having a trehalose structure are readily formed in a satisfactorily-high yield. Suspensions containing insoluble substrates can be used in the invention. The reaction temperature used in the present enzymatic reaction can be set to a temperature at which the present enzyme is not inactivated, i.e. a temperature up to about 55° C., preferably, a temperature in the range of 40–50° C. The reaction pH used in the present enzymatic reaction is controlled in the range of 5–10, preferably, in the range of about 6–8. The reaction time used in the present enzymatic reaction is adequately chosen dependently on the conditions of the enzymatic reaction.

The resultant reaction mixtures containing non-reducing saccharides have a reducing power much lower than those of the material reducing partial starch hydrolysates used as a substrate. For example, in the case of using maltopentaose as a substrate, about 93% of the initial reducing power diminishes or the reducing power lowers to about 7% with respect to the initial reducing power.

The resultant reaction mixtures are subjected to filtration and in conventional manner in order to remove insoluble substances, and the resultant solutions are decolored with an activated charcoal, desalted with ion exchangers in H- and OH-form, and concentrated into syrupy products. The syrupy products can be suitably dried into powdery products. If necessary, the powdery products can be readily prepared into non-reducing saccharides with the highest possible purity by purifying the powdery products with one or more methods, for example, column chromatographic fractionations such as ion-exchange column chromatography, column chromatography using an activated charcoal or a silica gel; separations using organic acids such as acetone and alcohol; and alkaline treatments to decompose and remove the remaining reducing saccharides.

More particularly, ion-exchange column chromatography can be suitably used in the invention as an industrial-scale preparation of the objective saccharides. The objective non-reducing saccharides with an improved purity can be arbitrarly prepared by, for example, column chromatography using a strongly-acidic cation exchange resin as described in Japanese Patent Laid-Open Nos.23,799/83 and 72,598/83 to remove concomitant saccharides. In this case, any one of fixed-bed, moving bed, and semi-moving methods can be employed.

If necessary, the present non-reducing saccharides having a trehalose structure or relatively-low reducing saccharides containing the non-reducing saccharides can be hydrolyzed by amylases such as α-amylase, β-amylase, glucoamylase and α-glucosidase in order to control their sweetness and reducing power or to lower their viscosity; and the resultant products can be further treated such that the remaining reducing saccharides are hydrogenated into sugar alcohols to diminish their reducing powder.

More particularly, trehalose is readily prepared by allowing glucoamylase or α-glucosidase to act on the present non-reducing saccharides or relatively-low reducing saccharides containing them. A high trehalose content fraction is obtained by allowing glucoamylase or α-glucosidase to act on these saccharides to form a mixture of trehalose and glucose, and subjecting the mixture to the aforementioned purifications such as ion-exchange column chromatography to remove glucose. The high trehalose content fraction can be arbitrary purified and concentrated into a syrupy product, and, if necessary, the syrupy product can be concentrated into a supersaturated solution, followed by crystallizing hydrous- or anhydrous-crystalline trehalose and recovering the resultant crystal.

In order to prepare hydrous crystalline trehalose, an about 65–90% solution of trehalose with a purity of about 60% or higher is placed in a crystallizer, and gradually cooled while stirring in the presence of 0.1–20% seed crystal at a temperature of 95° C. or lower, preferably, at a temperature in the range of 10–90° C., to obtain a massecuite containing hydrous crystalline trehalose. Conventional methods such as separation, block pulverization, fluidized-bed granulation and spray drying can be employed in the invention to prepare from the massecuite hydrous crystalline trehalose or crystalline saccharides containing it.

In the case of separation, massecuites are usually subjected to a basket-type centrifuge to separate hydrous crystalline trehalose from the mother liquor, and, if necessary the hydrous crystalline trehalose is washed by spraying with a small amount of cold water to facilitate the preparation of hydrous crystalline trehalose with an increased purity. In the case of spray drying, crystalline saccharides with no hygroscopicity or which are substantially free of hygroscopicity are readily prepared by spraying massecuites with a concentration of 70–85%, d.s.b., and a crystallinity of about 20–60%, d.s.b., from a nozzle by a high-pressure pump; drying the resultant products with a 60–100° C. hot air which does not melt the resultant crystalline powders; and aging the resultant powders for about 1–20 hours while blowing thereto heated to about 30–60° C. In the case of block pulverization, crystalline saccharides with no hygroscopocity or which are substantially free of hygroscopicity are readily prepared by allowing massecuites with a moisture content of 10–20% and a crystallinity of about 10–60%, d.s.b., to stand for about 0.1–3 days in order to crystallize and solidify the whole contents into blocks; and pulverizing or cutting the resultant blocks.

Although anhydrous crystalline trehalose can be prepared by drying hydrous crystalline trehalose to convert it into the anhydrous form, it is generally prepared by providing a concentrated solution of trehalose with a moisture content less than 10%; placing the solution in a crystallizer; keeping the solution in the presence of a seed crystal at a temperature in the range of 50–160° C., preferably, a temperature in the range of 80–140° C. under stirring conditions to obtain a massecuite containing anhydrous crystalline trehalose; and crystallizing and pulverizing anhydrous crystalline trehalose by conventional methods such as block pulverization, fluidized-bed granulation and spray drying.

The resultant non-reducing saccharides and relatively-low reducing saccharides containing them according to the present invention have a relatively-lower reducing power and a relatively-higher stability than those of the material reducing partial starch hydrolysates, and because of this these saccharides can be mixed and processed with other materials, especially, amino acids and amino acid-containing substances such as oligopeptides and proteins without a fear of causing an undesirable browning, smell and deterioration of the materials. Unlike reducing partial starch hydrolysates, these saccharides have a relatively-low reducing power and viscosity, and among these saccharides those with a relatively-low degree of glucose polymerization have a satisfactorily-higher quality and more mild sweetness than the hydrolysates.

The present non-reducing saccharides are hydrolyzed by amylases such as α-amylase derived from pancreas into relatively-low molecular weight non-reducing oligosaccharides or maltooligosaccharides, and these oligosaccharides are readily hydrolyzed by α-glucosidase and intestinal enzymes into glucose and trehalose molecules. The resultant trehalose is readily hydrolyzed by trehalase into glucoses. Thus, the present non-reducing saccharides and relatively-low reducing saccharides containing them, as well as trehalose, can be utilized as an energy source by the body when orally administered. These present saccharides and trehalose are not substantially fermented by dental carries-inducing microorganisms, and this renders them useful as a dental carries-preventing sweetener.

The present non-reducing saccharides and relatively-low reducing saccharides containing them, as well as trehalose, have a satisfiable stability and sweetness, and those in crystalline form can be arbitrarily used as a sugar coating material for tablets in combination with binders such as pullulan, hydroxyethyl starch and polyvinylpyrrolidone. These saccharides and trehalose have properties such as osmotic pressure-controlling ability, filler-imparting ability, gloss-imparting ability, moisture-retaining ability, viscosity-imparting ability, substantial no fermentability, ability to prevent retrogradation of gelatinized starch, and ability to prevent crystallization of other saccharides.

Anhydrous crystalline trehalose can be arbitrarily used as a desiccant for food products, cosmetics, pharmaceuticals, and their materials and intermediates, and can be readily formed into compositions in the form of powder, granule and tablet with a satisfactory stability and quality.

Thus, the present non-reducing saccharides and relatively-low reducing saccharides containing them, as well as trehalose prepared from these saccharides, can be arbitrarily used as a sweetener, taste-improving agent, quality-improving agent, stabilizer, excipient and desiccant in a variety of compositions such as food products, tobaccos, cigarettes, feeds, pet foods, cosmetics and pharmaceuticals.

The present non-reducing saccharides and relatively-low reducing saccharides containing them, as well as trehalose prepared from these saccharides, can be used intact as a seasoning for sweetening. If necessary, they can be used together with adequate amounts of one or more other sweeteners, for example, powdered syrup, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrocharcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

The present non-reducing saccharides and relatively-low reducing saccharides containing them, as well as a powdery or crystalline trehalose prepared from these saccharides, can be used intact, or, if necessary they can be mixed with an excipient, filler and binder and formed into granules, spheres, shot-rods, plates, cubes and tablets, prior to their use.

The present non-reducing saccharides, relatively-low reducing saccharides containing them, and trehalose prepared from these saccharides have the following features: (i) They have a sweetness which well harmonizes with other materials having sour-, acid-, salty-, bitter-, astringent- and delicious-tastes; and (ii) they are highly acid- and heat-resistant. Thus, they can be favorably used in food products in general as a sweetener, taste-improving agent and quality-improving agent.

The present non-reducing saccharides, relatively-low reducing saccharides containing them, and trehalose prepared from these saccharides can be used in seasonings such as amino acids, peptides, soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleic acid condiments, mixed seasoning, "mirin" (a sweet sake), "shin-mirin" (a synthetic mirin), table sugar and coffee sugar.

Also, the present non-reducing saccharides, relatively-low reducing saccharides containing them, and trehalose prepared from these saccharides can be freely used for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as synthetic sake, wine and liquors; soft drinks such as coffee, tea, cocoa, juice, carbonated beverage, sour milk beverage and beverage containing a lactic acid bacterium; instant food products such as instant pudding mix, instant hot cake mix and "sokuseki-shiruco" (an instant mix of adzuki-bean soup with rice cake) and instant soup mix; and beverages such as baby foods, foods for therapy, beverages supplemented with nutrition, peptide foods and frozen foods; as well as for improving the tastes and qualities of the aforementioned food-products.

The present non-reducing saccharides, relatively-low reducing saccharides containing them, and trehalose prepared from these saccharides can be also used in feeds and pet foods for animals such as domestic animals, poultry, honey bees, silk worms and fishes in order to improve their taste preferences. These saccharides and trehalose can be arbitrarily used as a sweetener, taste-improving agent, quality-improving agent and stabilizer in other products in paste and liquid form such as a tobacco, cigarette, dentifrice, lipstick, rouge, lip cream, internal medicine, tablet, troche, cod liver oil in the form of drop, cachou, oral refrigerant, gargle, cosmetic and pharmaceutical.

The present non-reducing saccharides, relatively-low reducing saccharides containing them, and trehalose prepared from these saccharides can be used as a quality-improving agent and stabilizer in biologically active substances which may contain unstable effective ingredients and activities, as well as in health foods and pharmaceuticals containing the biologically active substances. Examples of such a biologically active substance are lymphokines such as α-, β- and γ-interferons, tumor necrosis factor-α (TNF-α), tumor necrosis factor-β (TNF-β), macrophage migration inhibitory factor, colony-stimulating factor, transfer factor and interleukin 2; hormones such as insulin, growth hormone, prolactin, erythropoietin and follicle-stimulating hormone; biological preparations such as BCG vaccine, Japanese encephalitis vaccine, measles vaccine, live polio vaccine, smallpox vaccine, tetanus toxoid, Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, β-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as royal jelly. By using the present non-reducing saccharides, relatively-low reducing saccharides containing them, and trehalose prepared from these saccharides, the aforementioned biologically active substances are arbitrarily prepared into health foods and pharmaceuticals with a satisfactorily-high stability and quality without a fear of losing or inactivating their effective ingredients and activities.

As described above, the methods for incorporating the present non-reducing saccharides, relatively-low reducing saccharides containing them and/or trehalose prepared from these saccharides into the above-mentioned compositions include conventional methods, for example, mixing, kneading, dissolving, melting, soaking, permeating, sprinkling, applying, coating, spraying, injecting, crystallizing and solidifying. These saccharides and trehalose are usually incorporated into the above-mentioned compositions in an amount of 0.1% or higher, preferably, one % or higher, d.s.b.

The following experiments explain the present invention more in detail.

Firstly, producing, purification and properties of a non-reducing saccharide-forming amylase derived from a novel microorganism of Rhizobium sp. M-11 is described; and secondary, a non-reducing saccharide-forming enzyme derived from a microorganism of Arthrobacter sp. Q36 is similarly described as in the microorganism of Rhizobium sp. M-11. Thirdly, non-reducing saccharide-forming enzymes derived from hitherto known microorganisms are explained.

Experiment 1

Production of Non-reducing Saccharide-forming Enzyme from Rhizobium sp. M-11

A liquid nutrient culture medium, consisting of 2.0 w/v % maltose, 0.5 w/v % peptone, 0.1 w/v % yeast extract, 0.1 w/v % disodium hydrogenphosphate, 0.1 w/v % potassium hydrogenphosphate and water, was adjusted to pH 7.0. About 100 ml aliquots of the nutrient culture medium were placed in 500-ml Erlenmeyer flasks, autoclaved at 120° C. for 20 minutes to effect sterilization, cooled, inoculated with a stock culture of Rhizobium sp. M-11 (FERM BP-4130), and incubated at 27° C. for 24 hours under stirring conditions of 130 rpm. The resultant cultures were pooled and used as a seed culture.

About 20 L of a fresh preparation of the same nutrient culture medium used in the above culture was placed in a 30-L fermentor, sterilized, cooled to 30° C., inoculated with one w/v % of the seed culture, and incubated for about 24 hours while stirring under aerobic conditions at 30° C. and pH 6.0–8.0. The resultant culture had an enzyme activity of about 1.5 units/ml. A portion of the culture was centrifuged to separate cells and culture supernatant, and the cells were suspended in 50 mM phosphate buffer (pH 7.0) to give the original volume of the portion, followed by assaying enzyme activities of the cell suspension and culture supernatant to give about 0.6 units/ml and about 0.9 units/ml respectively.

Experiment 2
Purification of Enzyme

An about 18 L of the culture obtained in Experiment 1 was treated with "Mini-Rabo", a super high-pressure cell disrupting apparatus commercialized by Dainippon Pharmaceutical Co., Ltd., Tokyo, Japan, to disrupt cells. The resultant mixture was centrifuged at 10,000 rpm for 30 minutes to obtain about 16 L supernatant. To the supernatant was added ammonium sulfate and dissolved to give a saturation degree of 0.2, and the resultant solution was allowed to stand at 4° C. for one hour, and centrifuged at 10,000 rpm for 30 min to obtain a supernatant.

Ammonium sulfate was dissolved in the supernatant to give a saturation degree of 0.6, and the resultant solution was centrifuged at 10,000 rpm for 30 min to obtain a precipitate. The resultant precipitate was dissolved in 10 mM phosphate buffer (pH 7.0), and the resultant solution was dialyzed against a fresh preparation of the same phosphate buffer for 24 hours, and centrifuged at 10,000 rpm for 30 min to remove insoluble substances. Three hundred and sixty ml of the resultant dialyzed solution was divided into 2 portions which were then separately subjected to column chromatography using a column packed with 300 ml of "DEAE-Toyopearl®", an ion exchanger commercialized by Tosoh Corporation, Tokyo, Japan.

The objective enzyme was adsorbed on the ion exchanger, and eluted from the column with a fresh preparation of the same phosphate buffer supplemented with salt. The resultant fractions having the objective enzyme activity were pooled, and dialyzed against a fresh preparation of the same phosphate buffer supplemented with 2M ammonium sulfate. The dialyzed solution thus obtained was centrifuged at 10,000 rpm for 30 min to remove insoluble substances, and the resultant supernatant was subjected to hydrophobic column chromatography using a column packed with 300 ml of "Butyl-Toyopearl® 650", a hydrophobic gel commercialized by Tosoh Corporation, Tokyo, Japan. The enzyme adsorbed on the gel was eluted from the column with a liner gradient buffer from 2M to 0M, followed by recovering fractions with the enzyme activity. The resultant fractions were subjected to gel filtration chromatography using "Toyopearl® HW-55", a resin for gel chromatography commercialized by Tosoh Corporation, Tokyo, Japan, followed by recovering fractions with the enzyme activity. The enzyme activity, specific activity and yield in each purification step are as shown in Table 1.

TABLE 1

| Purification step | Enzyme activity (unit) | Specific activity (units/mg protein) | Yield (%) |
| --- | --- | --- | --- |
| Culture | 26,800 | | 100 |
| Supernatant after cell disruption | 20,300 | 0.10 | 76 |
| Dialyzed solution after salting out with ammonium sulfate | 16,100 | 0.32 | 60 |
| Eluate from ion-exchange column | 11,300 | 5.5 | 42 |
| Eluate from hydropbobic column | 5,730 | 98 | 21 |
| Eluate from gel filtration column | 3,890 | 195 | 15 |

A purified enzyme preparation, obtained as an eluate from gel filtration column in Table 1, was essayed for purity on electrophoresis using 7.5% polyacrylamide gel to exhibit a single protein band, and this essay revealed that the preparation was an electrophoretically homogeneous enzyme with a relatively-high purity.

Experiment 3
Property of Enzyme

The purified enzyme preparation obtained in Experiment 2 was subjected to electrophoresis using 10% sodium dodecylsulfate polyacrylamide gel, and this revealed that the molecular weight was about 77,000–87,000 daltons in comparison with those of marker proteins commercialized by Japan Bio-Rad Laboratories, Tokyo, Japan.

The purified enzyme preparation was subjected to isoelectrophoresis using polyacrylamide gel containing 2 v/v % "Ampholine" an ampholyte commercialized by Pharmacia LKB Biotechnology AB, Uppsala, Sweden. The resultant gel was sliced into pieces, and a gel piece containing the enzyme was essayed and revealed that the enzyme has a pI of about 3.6–4.6.

Figure 2:
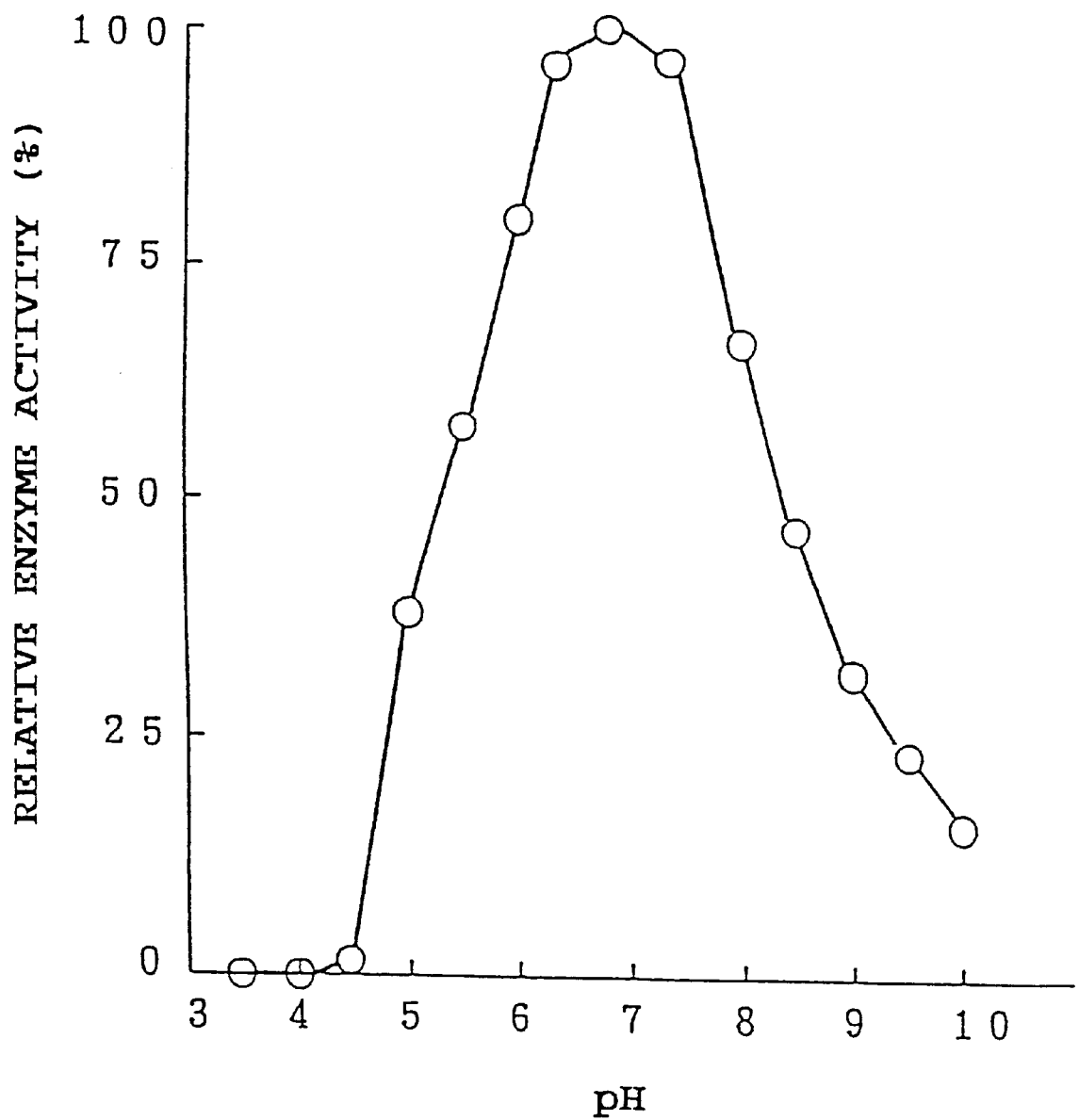
FIG. 2 shows the influence of pH on the activity of non-reducing saccharide-forming enzyme derived from Rhizobium sp. M-11.
Figure 3:
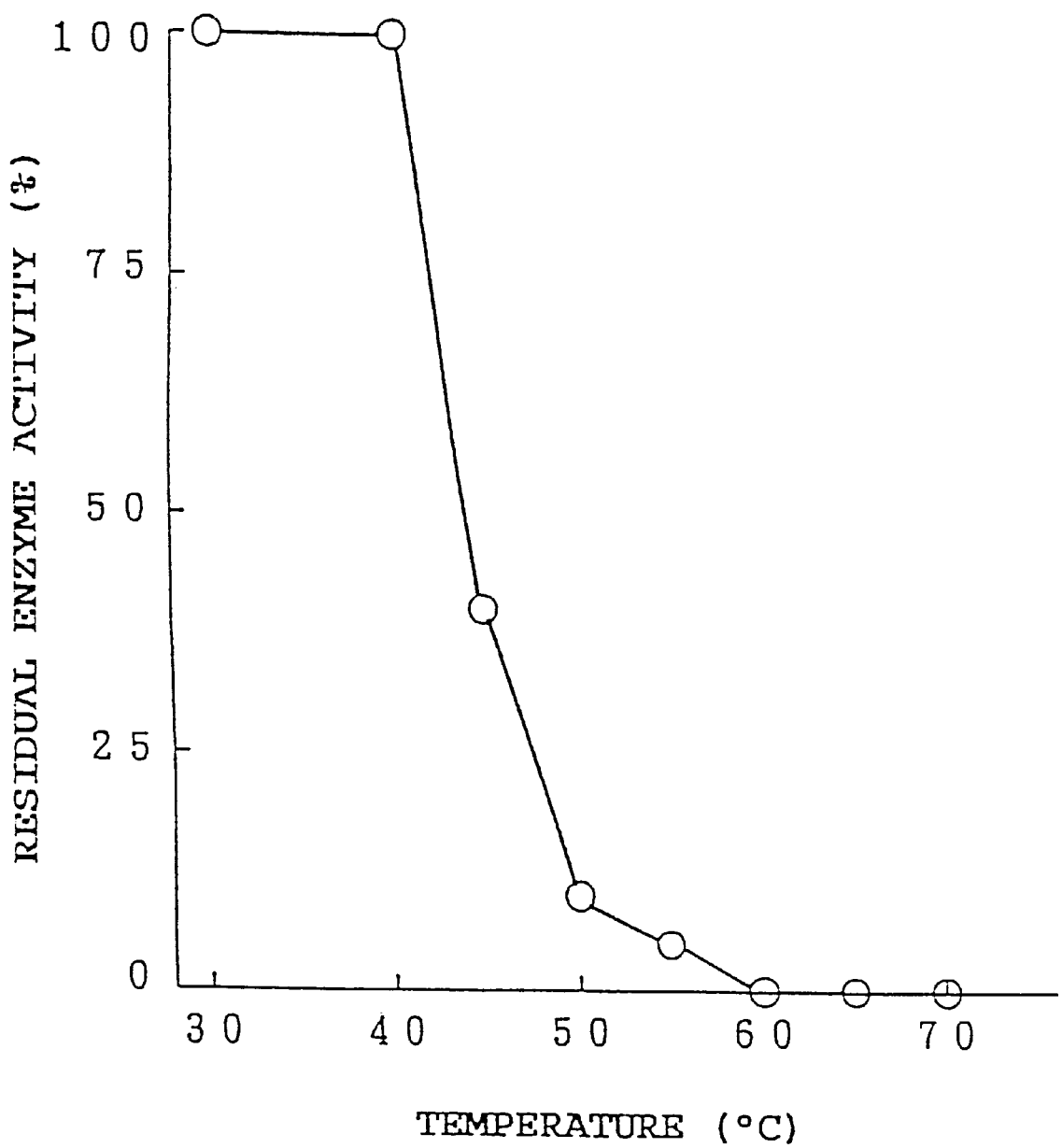
FIG. 3 shows the thermal stability of non-reducing saccharide-forming enzyme derived from Rhizobium sp. M-11.
Figure 4:
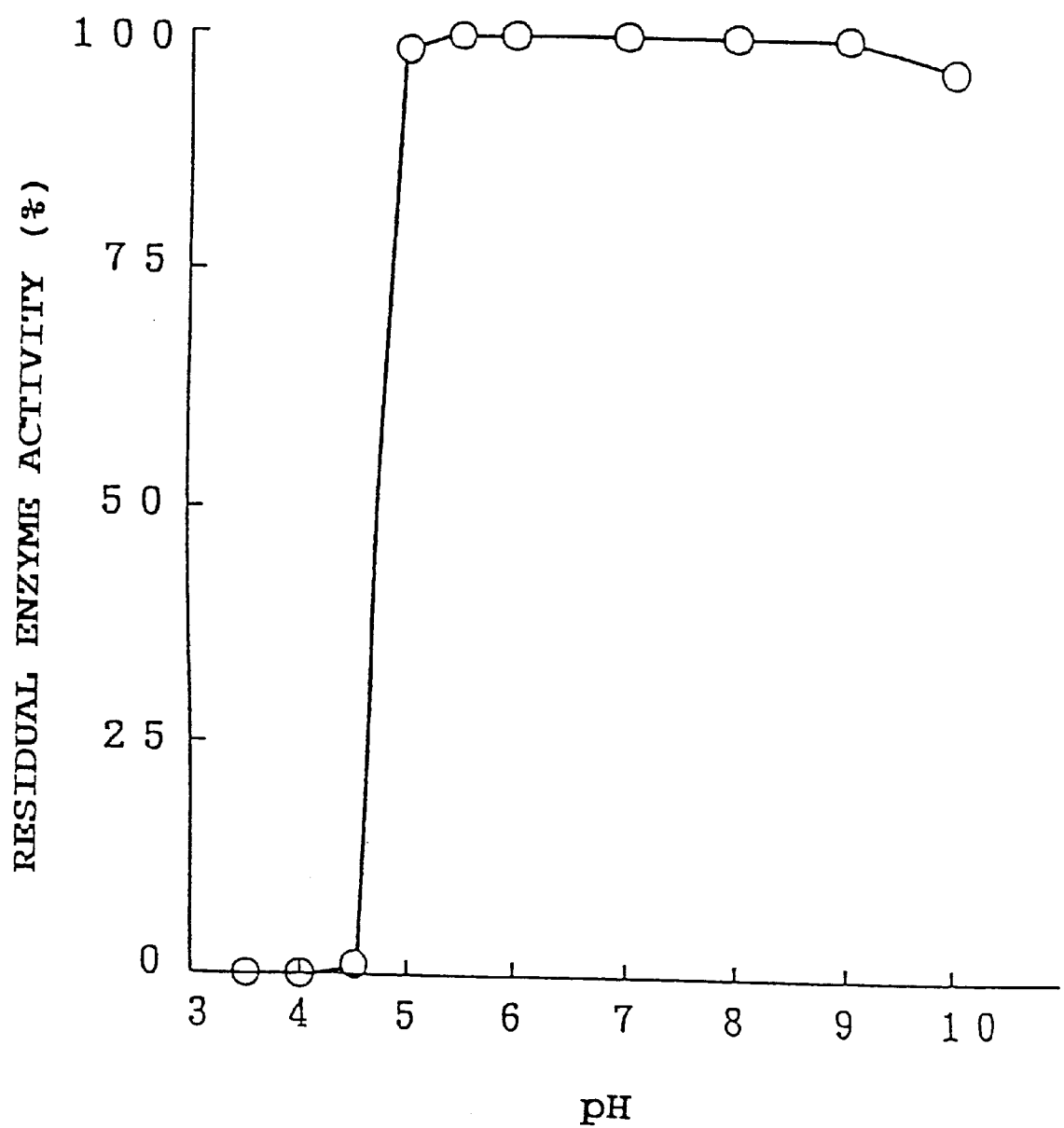
FIG. 4 shows the pH stability of non-reducing saccharide-forming enzyme derived from Rhizobium sp. M-11.
Figure 5:
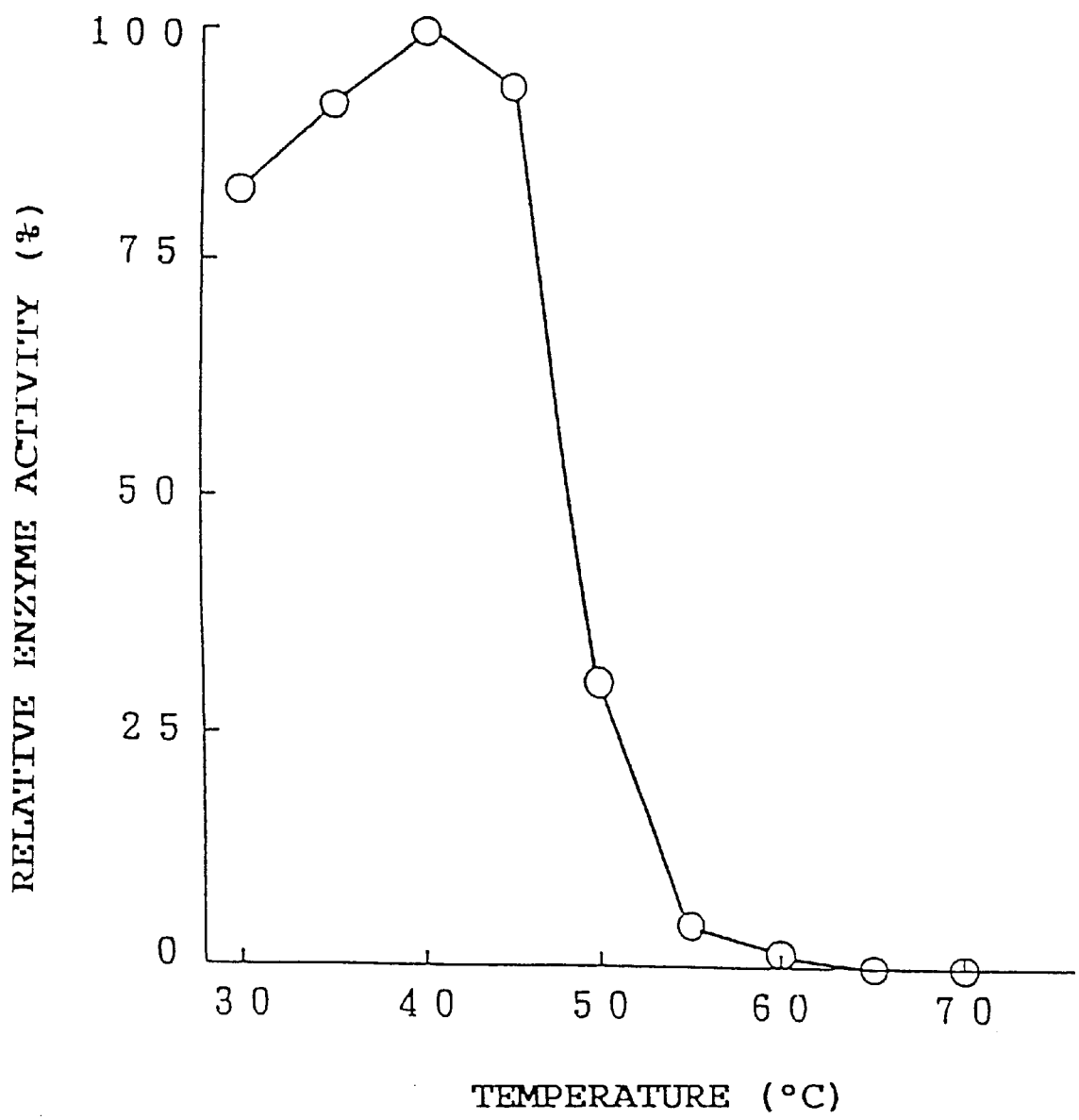
FIG. 5 shows the influence of temperature on the activity of non-reducing saccharide-forming enzyme derived from Arthrobacter sp. Q36.
Figure 6:
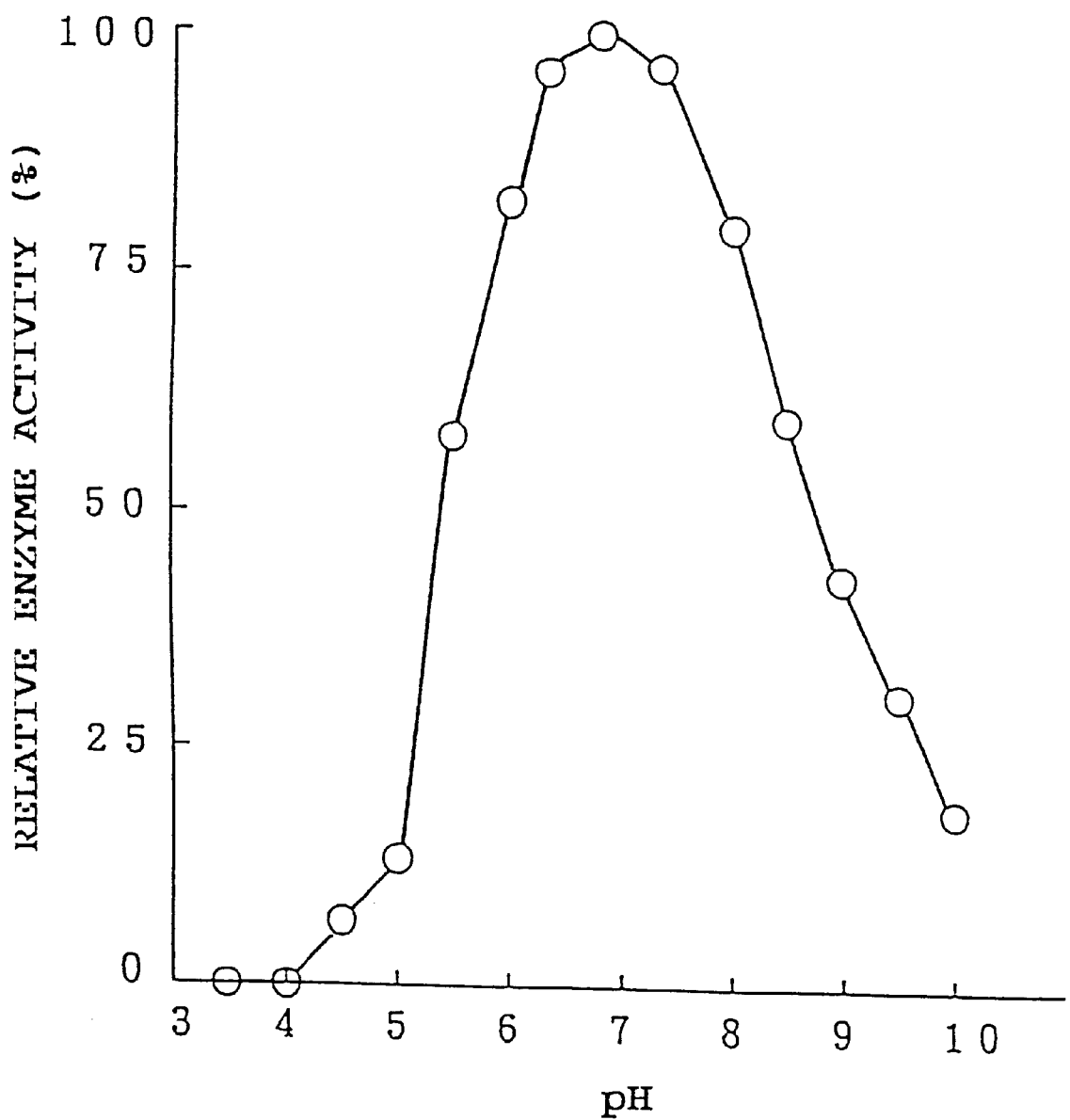
FIG. 6 shows the influence of pH on the activity of non-reducing saccharide-forming enzyme derived from Arthrobacter sp. Q36.
Figure 7:
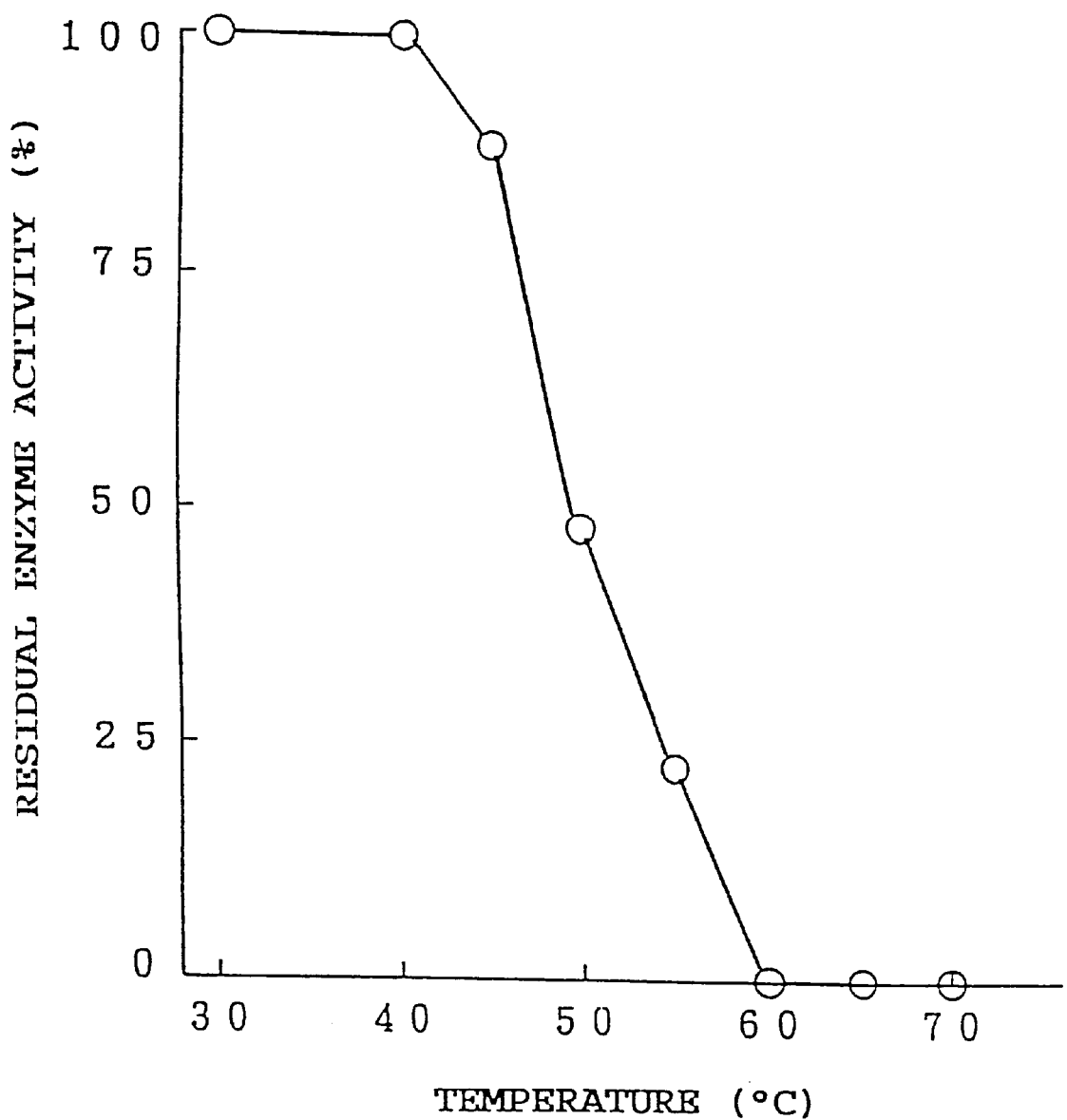
FIG. 7 shows the thermal stability of non-reducing saccharide-forming enzyme derived from Arthrobacter sp. Q36.
Figure 8:
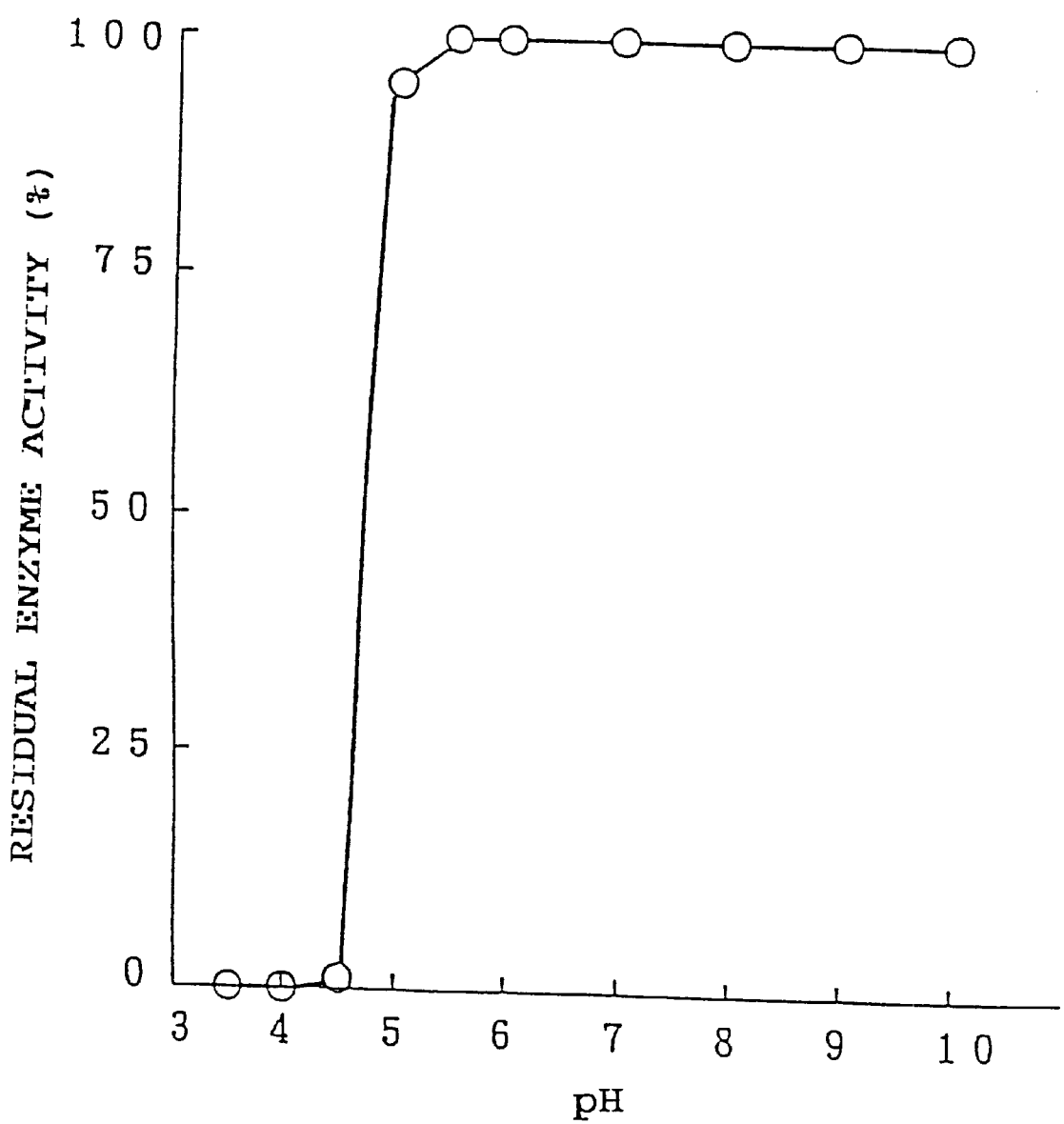
FIG. 8 shows the pH stability of non-reducing saccharide-forming enzyme derived from Arthrobacter sp. Q36.

Effects of temperature and pH on the enzyme were studied in accordance with the assay as used for the enzyme activity. These results were respectively shown in FIGS. 1 and 2. The optimum temperature of the enzyme was about 40° C. when reacted at pH 7.0 for 60 min, and the optimum pH was about 7.0 when reacted at 40° C. for 60 min. The thermal stability of the enzyme was determined by incubating it in 50 mM phosphate buffers (pH 7.0) at different temperatures for 60 min, cooling the buffers, and assaying the remaining enzyme activity in each buffer. The pH stability of the enzyme was determined by incubating it in 50 mM phosphate buffers having different pHs at 25° C. for 16 hours, adjusting the buffers to pH 7, and assaying the remaining enzyme activity in each buffer. The results of thermal stability and pH stability were respectively shown in FIGS. 3 and 4. The enzyme was stable up to a temperature of about 40° C. and at a pH of about 6–9.

Experiment 4
Preparation of Non-reducing Saccharides

An aqueous solution containing 20% glucose, maltose, maltotriose, maltotetraose, maltopentaose, maltohexaose or maltoheptaose as a substrate was prepared, and mixed with 2 units per g substrate, d.s.b., of the purified enzyme preparation obtained in Experiment 2, and the resultant mixture was subjected to an enzymatic reaction at 40° C. and pH 7.0 for 48 hours. The reaction mixture was desalted and analyzed on high-performance liquid chromatography (HPLC) using "Wakobeads WB-T-330 column", a product of Wako Pure Chemical Industries Ltd., Tokyo, Japan. The HPLC procedure was conducted at an ambient temperature and a flow rate of 0.5 ml/min of water as an eluent, and "RI-8012", a differential refractometer commercialized by Tosho Corporation, Tokyo, Japan, was used for analyzing reaction products.

The results were as shown in Table 2.

TABLE 2

| Substrate | Product | Elution time on HPLC (min) | Percentage (%) |
|---|---|---|---|
| Glucose | Glucose | 33.4 | 100.0 |
| Maltose | Maltose | 28.5 | 100.0 |
| Maltotriose | P I | 23.3 | 35.0 |
| | Maltotriose | 25.9 | 65.0 |
| Maltotetraose | P II | 21.6 | 85.6 |
| | Maltotetraose | 24.1 | 14.4 |
| Maltopentaose | P III | 19.7 | 92.7 |
| | Maltopentaose | 22.6 | 7.3 |
| Maltohexaose | P IV | 18.7 | 93.5 |
| | Maltohexaose | 21.4 | 6.5 |
| Maltoheptaose | P V | 17.8 | 93.4 |
| | Maltoheptaose | 21.0 | 6.7 |

Note: In the Table, the symbols "P I", "P II", "P III", "P IV" and "P V" mean novel saccharides formed from the respective substrates of maltotriose, maltotetraose, maltopentaose, maltohexaose and maltoheptaose.

As evident from the results in Table 2, each reaction product substantially consisted of the remaining substrate and a newly-formed saccharide P I, P II, P III, P IV or P V, and other saccharides were not substantially detected. It was revealed that P II, P III, P IV and P V, which have a degree of glucose polymerization of 4 or higher, gave a high yield, i.e. a percentage of 85% or higher, d.s.b., while the yield of P I, which has a degree of glucose polymerization of 3 or higher, gave a relatively-low yield. It was revealed that no novel saccharide was formed from glucose and maltose.

In order to purify the newly-formed saccharides in each reaction mixture, they were column chromatographed on "XT-1016 (Na+-form, polymerization degree of 4%)", an alkaline-metal strongly-acidic action exchange resin commercialized by Tokyo organic Chemical Industries, Ltd., Tokyo, Japan. The resin was packed in 3 jacketed-stainless steel columns, each column having an inner diameter of 2.0 cm and a length of one m, and the columns were cascaded in series, fed with a 5 v/v % reaction mixture containing saccharides against the resin while the inner column temperature was keeping at 55° C., and eluted with 55° C. hot water at a flow rate of SV (space velocity) 0.13 to obtain a high-purity saccharide fraction containing 97% or higher of a novel saccharide, d.s.b. The fraction was dried in vacuo to obtain a high-purity preparation of a novel saccharide. The yields of P I, P II, P III, P IV and P IV were respectively about 9%, 65%, 82%, 80% and 77% with respect to their material saccharides, d.s.b. The purities of P I, P II, P III, P IV and P V were respectively about 97.5%, 98.6%, 99.5%, 98.4% and 98.4%, d.s.b.

The reducing powders of these novel saccharides were determined on the Somogyi-Nelson's method and expressed by DE (dextrose equivalent). The results were as shown in Table 3.

TABLE 3

| Saccharide preparation | Purity (%) | DE |
|---|---|---|
| P I | 97.5 | 0.83 |
| P II | 98.6 | 0.35 |

TABLE 3-continued

| Saccharide preparation | Purity (%) | DE |
|---|---|---|
| P III | 99.5 | 0.10 |
| P IV | 98.4 | 0.27 |
| P V | 98.4 | 0.23 |

As evident from the results in Table 3, each saccharide preparation only showed a slight reducing power. It was estimated that the slight reducing power was due to the remaining reducing maltooligosaccharides originally present in the substrates, and this led to a conclusion that the newly formed saccharides were substantially non-reducing saccharides.

Experiment 5

Maillard Reaction

A solution, containing of one % glycine and 10% of a saccharide preparation P I, P II, P III, P IV or P V in Experiment 4 and 50 mM phosphate buffer (pH 7.0), was kept at 100° C. for 90 min, followed by cooling the resultant solution, and determining its absorbance at a wave length of 480 nm in 1-cm cell. As a control, maltotriose, maltotetraose, maltopentaose, maltohexaose and maltoheptaose as a material for the saccharide preparations were similarly treated as above, and measured their absorbances were measured at a wave length of 480 nm. The results were as shown in Table 4.

TABLE 4

| Saccharide preparation | Coloration degree (480 nm) | Judgement |
|---|---|---|
| P I | 0.027 | Present invention |
| P II | 0.018 | Present invention |
| P III | 0.012 | Present invention |
| P IV | 0.016 | Present invention |
| P V | 0.015 | Present invention |
| Maltotriose | 0.623 | Control |
| Maltotetraose | 0.475 | Control |
| Maltopentaose | 0.369 | Control |
| Maltohexaose | 0.318 | Control |
| Maltoheptaose | 0.271 | Control |

As evident from the results in Table 4, it was revealed that the newly-formed non-reducing saccharides P I, P II, P III, P IV and P V only showed a slight coloration caused by the maillard reaction, i.e. the coloration degree was only 3–6% of those of their corresponding material maltooligosaccharides. The results revealed that the non-reducing saccharides formed by the present enzyme are substantially free from the maillard reaction.

Experiment 6

Enzymatic Hydrolysis by Glucoamylase

Fifty mg aliquots of non-reducing saccharides P I, P II, P III, P IV and P V in Experiment 4 were respectively dissolved in one ml of 50 mM acetate buffer (pH 4.5), admixed with one unit of glucoamylase commercialized by Seikagaku-Kogyo Co., Ltd., Tokyo, Japan, to effect enzymatic hydrolysis at 40° C. for 6 hours. The only saccharides detected in every resultant mixture on HPLC analysis were glucose and trehalose. The contents of the detected glucose and trehalose, and their molecular ratios were as shown in Table 5.

TABLE 5

| Saccharide preparation | Glucose (%) | Trehalose (%) | Molecular ratio (Glucose/Trehalose) |
|---|---|---|---|
| P I | 36.2 | 63.8 | 1.07 |
| P II | 52.0 | 48.0 | 2.06 |
| P III | 61.4 | 38.6 | 3.02 |
| P IV | 68.3 | 31.7 | 4.09 |
| P V | 72.9 | 27.1 | 5.11 |

As evident from the results in Table 5, it was revealed that (i) the non-reducing saccharide P I was hydrolyzed into one mole of glucose and one mole of trehalose; P II, hydrolyzed into two moles of glucose and one mole of trehalose; (iii) P III, hydrolyzed into three moles of glucose and one mole of trehalose; (iv) P IV, hydrolyzed into four moles of glucose and one mole of trehalose; and (v) P V, hydrolyzed into five moles of glucose and one mole of trehalose.

In view of the enzymatic reaction mechanism of glucoamylase, it was revealed that these non-reducing saccharides have a structure of saccharide consisting of one or more moles of glucose bound to one mole of trehalose via the α-1,4 linkage or α-1,6 linkage: The non-reducing saccharide P I is a non-reducing saccharide having a degree of glucose polymerization of 3 (DP 3) and consisting of one mole of glucose bound to one mole of trehalose; P II, a non-reducing saccharide having DP 4 and consisting of two moles of glucose bound to one mole of trehalose; P III, a non-reducing saccharide having DP 5 and consisting of three moles of glucose bound to one mole of trehalose; P IV, a non-reducing saccharide having DP 6 and consisting of four moles of glucose bound to one mole of trehalose; and P V, a non-reducing saccharide having DP 7 and consisting of five moles of glucose bound to one mole of trehalose. It was revealed that, when β-amylase was act on these non-reducing saccharides similarly as with glucoamylase, P I and P II were not hydrolyzed but P III, P IV and P V were respectively hydrolyzed into one mole of maltose and one mole of P I, one mole of maltose and one mole of P II, and two moles of maltose and one mole of P I.

Based on these results, it was concluded that the enzymatic reaction of the present non-reducing saccharide-forming enzyme is an intramolecular reaction without changing the molecular weights of the substrates used, i.e. an intramolecular reaction without changing their degrees of glucose polymerization. It was concluded that the non-reducing saccharides P I, P II, P III, P IV and P V were the respective α-glycosyl trehaloses ($G_n$-T, wherein the symbol "G" means glucose residue; the symbol "n", one or more integers; and the symbol "T", α,α-trehalose residue) of α-glucosyl trehalose, α-maltosyl trehalose, α-maltotriosyl trehalose, α-maltotetraosyl trehalose and α-maltopentaosyl trehalose.

Experiment 7
Hydrolysis by Enzymes

The non-reducing saccharide P I, P II, P III, P IV or P V as a substrate in Experiment 4 was subjected to an α-amylase specimen derived from pig pancreas, an α-glucosidase specimen derived from rice or a rat intestinal acetone powder, all of which are commercialized by Sigma Chemical Company, St. Louis, USA, and each resultant hydrolysate was analyzed on HPLC to reveal its saccharide composition. The enzymatic reaction with the α-amylase was as follows: Dissolving 10 mg of a substrate in one ml of 50 mM phosphate buffer (pH 6.9), mixing the resultant solution with one unit of the α-amylase, and incubating the resultant mixture at 37° C. for 18 hours. The enzymatic reaction with the α-glucosidase was conducted under the same conditions as in the case of α-amylase except that 50 mM acetate buffer (pH 4.0) was used as a buffer. The enzymatic reaction with the rat intestinal acetone powder was carried out under the same conditions as in the case of α-amylase except that 50 mM maleate buffer (pH 6.0) was used as a buffer. The saccharide compositions obtained with the α-amylase, α-glucosidase and rat intestinal acetone powder were as shown in tables 6, 7 and 8 in this order.

TABLE 6

| | Saccharide composition of hydrolysate | | | | |
|---|---|---|---|---|---|
| Saccharide | P I | P II | G3 | G2 | G1 |
| P I | 97.3 | 0 | 2.3 | 0.4 | 0 |
| P II | 0 | 98.8 | 0.4 | 0.8 | 0 |
| P III | 61.0 | 4.8 | 0 | 33.0 | 1.2 |
| P IV | 47.2 | 3.3 | 40.4 | 7.5 | 1.6 |
| P V | 10.2 | 44.9 | 35.3 | 8.6 | 1.0 |

Note: In the table, the symbols "G3", "G2" and "G1" means maltotriose, maltose and glucose respectively.

TABLE 7

| | Saccharide composition of hydrolysate with α-glucosidase | | |
|---|---|---|---|
| Saccharide | Glucose (%) | Trehalose (%) | Other saccharides (%) |
| P I | 36.5 | 63.0 | 0.5 |
| P II | 52.1 | 47.6 | 0.3 |
| P III | 61.7 | 38.1 | 0.2 |
| P IV | 69.5 | 30.2 | 0.3 |
| P V | 71.4 | 28.3 | 0.3 |

TABLE 8

| | Saccharide composition of hydrolysate with rat intestinal acetone powder | | |
|---|---|---|---|
| Saccharide | Glucose (%) | Trehalose (%) | Other saccharides (%) |
| P I | 37.2 | 62.4 | 0.4 |
| P II | 52.5 | 47.1 | 0.4 |
| P III | 62.0 | 37.6 | 0.4 |
| P IV | 68.8 | 30.8 | 0.4 |
| P V | 73.4 | 26.5 | 0.1 |

As evident from the Table 6, it was revealed that the saccharide preparations P I and P II were not substantially hydrolyzed by α-amylase, while the saccharide preparations P III, P IV and P V were hydrolyzed by α-amylase into lower molecular weight oligosaccharides, P I, P II, maltotriose, maltose and glucose.

As evident from the results in Tables 7 and 8, it was revealed that similarly as in Experiment 6 with glucoamylase the saccharide preparations P I, P II, P III, P IV and P V were hydrolyzed by α-glucosidase and rat intestinal acetone powder into glucose and trehalose molecules.

To the resultant hydrolysate obtained with α-glucosidase or rat intestinal acetone powder was added one unit trehalase derived from pig kidney, an enzyme preparation of Sigma Chemical Company, St. Louis, USA, and the mixture was incubated at pH 5.7 and 37° C. for 18 hours, followed by analyzing the saccharide composition of the resultant mixture on HPLC to reveal that trehalose, formed from the saccharide preparations P I, P II, P III, P IV and P V, was hydrolyzed by trehalase into glucose molecules.

These observations are summarized as follows:

(1) The present non-reducing saccharide-forming enzyme forms non-reducing saccharides having a trehalose structure when allowed to act on one or more reducing partial starch hydrolysates having a degree of glucose polymerization of 3 or higher without changing their degrees of glucose polymerization; and (2) The non-reducing saccharide P V is mainly hydrolyzed by α-amylase into the non-reducing saccharide P II and maltotriose, while the non-reducing saccharide P II is hydrolyzed by glucoamylase into one mole of trehalose and two moles of glucose.

Based on these results, it was concluded that the present non-reducing saccharide-forming enzyme is a novel enzyme which intramolecularly converts a reducing end unit in reducing partial starch hydrolysates to a non-reducing end unit, a trehalose residue, i.e. a trehalose structure.

Experiment 8

Acute Toxicity Test

By using 7-week old dd-strain mice, the non-reducing saccharide preparation P I, P II, P III, P IV or P V was orally administered to the mice for its acute toxicity test. As a result, it was revealed that these saccharide preparations are safe substances with a relatively-low toxicity, and that no mouse died even when administered them at the highest possible doses. Though not so accurate, the values of $LD_{50}$ of these saccharide preparations were 50 g/kg or higher.

Experiment 9

Production of Non-reducing Saccharide-forming Enzyme from Arthrobacter sp. Q36

Similarly as in Experiment 1, a seed culture of Arthrobacter sp. Q36 (FERM BP-4316) was cultured by a fermentor for about 72 hours in place of Rhizobium sp. M-11 (FERM BP-4130). The enzymatic activity of a non-reducing saccharide-forming enzyme in the resultant culture was about 1.2 units/ml. Similarly as in Experiment 1, a cell suspension and a supernatant, prepared from the resultant culture, were assayed for their activities to give about 0.5 units/ml and about 0.7 units/ml respectively.

Experiment 10

Purification of Enzyme

By using about 18 L of the resultant culture obtained by the method in Experiment 9, the resultant non-reducing saccharide-forming enzyme was purified similarly as in Experiment 2. The results in each purification step were tabulated in Table 9.

TABLE 9

| Purification step | Enzyme* activity (unit) | Specific activity (units/mg protein) | Yield (%) |
| --- | --- | --- | --- |
| Culture | 21,600 | | 100 |
| Supernatant after cell disruption | 17,500 | 0.14 | 81 |
| Dialyzed solution after salting out with ammonium sulfate | 15,700 | 0.41 | 73 |
| Eluate from ion-exchange column | 12,600 | 6.5 | 58 |
| Eluate from hydrophobic column | 8,820 | 98 | 41 |
| Eluate from gel filtration column | 5,290 | 201 | 24 |

Note: The symbol "*" means a non-reducing saccharide-forming enzyme.

A purified enzyme preparation, obtained as the eluate from gel filtration column in Table 9, was studied for purity on electrophoresis similarly as in Experiment 2 to reveal a single protein band, and this showed that the enzyme preparation was a relatively-high purity enzyme having an electrophoretically single band.

Experiment 11

Property of Enzyme

The purified enzyme preparation obtained in Experiment 10 was determined its molecular weight on SDS-PAGE to give about 76,000–86,000 daltons. The pI of the enzyme preparation was determined on isoelectrophoresis similarly as in Experiment 3 to give a pI of about 3.6–4.6. The effects of temperature and pH on the enzyme preparation, and the thermal stability and pH stability thereof were studied similarly as in Experiment 3. These results on temperature, pH, thermal stability and pH stability were respectively as shown in FIGS. 5, 6, 7 and 8.

As evident from these Figures, the optimum temperature of the enzyme preparation is about 40° C.; the optimum pH, about 6.5–7.0; the thermal stability, up to about 40° C.; and the pH stability, about 6.0–9.5.

Experiment 12

Preparation of Non-reducing Saccharide

By using the purified enzyme preparation obtained in Experiment 10, the preparation and the confirmation of the structure of non-reducing saccharides were conducted in accordance with the methods in Experiments 4 and 6. As a result, it was revealed that the enzyme preparation forms one or more non-reducing saccharides, which saccharide has a trehalose structure as an end unit and a degree of glucose polymerization of 3 or higher, when allowed to act on one or more reducing partial starch hydrolysates having a degree of glucose polymerization of 3 or higher.

Experiment 13

Preparation and Property of Non-reducing Saccharide-forming Enzyme from known Microorganisms Among known microorganisms the microorganisms as listed in Table 10, which had been confirmed to produce the present non-reducing saccharide-forming enzyme, were cultured by a fermentor at 27° C. for 72 hours similarly as in Experiment 1 except that a microorganism of *Mycobacterium smegmatis* (ATCC 19420) was cultured at 37° C. Eighteen L of each resultant culture was subjected to a cell disrupting apparatus, and the resultant supernatant was salted out with ammonium sulfate, dialyzed, and subjected to an ion-exchange column to obtain a partially purified enzyme preparation, followed by studying its properties.

The results were tabulated in Table 10.

TABLE 10

| Microorganism | Enzyme activity in eluate from ion-exchange column (Unit) | Optimum temperature (° C.) | Optimum pH (° C.) | Thermal stability | pH Stability |
|---|---|---|---|---|---|
| Brevibacterium helovolum (ATCC 11822) | 2,700 | About 35 | About 6.5 | Up to about 35 | About 5.5–11.0 |
| Flavobacterium aquatile (IFO 3772) | 216 | About 35 | About 6.5–6.9 | Up to about 35 | About 6.0–9.5 |
| Micrococcus luteus (IFO 3064) | 1,730 | About 35 | About 6.4–6.8 | Up to about 35 | About 6.5–8.0 |
| Micrococcus roseus (ATCC 186) | 1,340 | About 35 | About 6.8–7.2 | Up to about 35 | About 6.0–11.0 |
| Curtobacterium citreum (IFO 15231) | 1,290 | About 30 | About 6.4–6.8 | Up to about 35 | About 6.5–7.8 |
| Mycobacterium smegmatis (ATCC 19420) | 358 | About 35 | About 6.5 | Up to about 35 | About 6.0–9.0 |
| Terrabacter tumescens (IFO 12960) | 1,050 | About 35 | About 6.5–7.0 | Up to about 35 | About 6.0–9.5 |
| Rhizobium sp. M-11 (FERM BP-4130) | 11,300 | About 40 | About 7.0 | Up to about 40 | About 6.0–9.0 |
| Arthrobacter sp. Q36 (FERM BP-4316) | 12,600 | About 40 | About 6.5–7.0 | Up to about 40 | About 6.0–9.5 |

In accordance with the method in Experiment 12, non-reducing saccharides were prepared by using partially purified enzyme preparations from these known microorganisms, and their structures were studied to find that, similarly as the non-reducing saccharide-forming enzyme from Rhizobium sp. M-11, every enzyme preparation formed non-reducing saccharides having a trehalose structure as an end unit and a degree of glucose polymerization of 3 or higher when allowed to act on one or more reducing partial starch hydrolysates having a degree of glucose polymerization of 3 or higher.

Experiment 14
Partial Amino Acid Sequence of Non-reducing Saccharide-forming Enzyme

Experiment 14 (1)
Amino Acid Sequence Containing N-terminal

A part of a purified enzyme preparation derived from Rhizobium sp. M-11, obtained by the method in Experiment 2, and a part of a purified enzyme preparation derived from Arthrobacter sp. Q36, obtained by the method in Experiment 10, were dialyzed against distilled water, and about 80 μg protein of each resultant preparation was used as a sample for determining their amino acid sequences containing their N-terminals. The amino acid sequences were analyzed on "Protein sequencer Model 473A", an apparatus of Applied Biosystems, Inc., Foster City, USA, to reveal their 10 amino acid residues from their N-terminals. Partial amino acid sequences containing the N-terminals of the enzyme preparations were as shown in Table 11.

TABLE 11

| Origin | Partial amino acid sequence containing N-terminal |
|---|---|
| Rhizobium sp. M-11 | valine (or methionine)-arginine-threonine-proline-alanine-serine-threonine-tyrosine-arginine-leucine- |
| Arthrobacter sp. Q36 | methionine-arginine-threonine-proline-valine-serine-threonine-tyrosine-arginine-leucine- |

As evident from Table 11, the partial amino acid sequence containing the N-terminal of the enzyme preparation from Rhizobium sp. M-11 differs from that of Arthrobacter sp. Q36 in that the N-terminal amino acid residue of the former is valine or methionine and that of the latter is methionine, while they have 8 common amino acid residues among the analyzed 10 amino acid residues. More particularly, they completely coincide with each other in that they have the same amino acid sequence consisting of 3 amino acid residues which are positioned between L-arginine corresponding to the second amino acid residue with respect to their N-terminals and L-proline corresponding to the forth amino acid residue with respect to their N-terminals; as well as having the same amino acid sequence consisting of 5 amino acid residues which are positioned between L-serine corresponding to the sixth amino acid residue with respect to their N-terminals and L-leucine corresponding to the tenth amino acid residue with respect to their N-terminals. It was revealed that these enzyme preparations have a common partial amino acid sequence containing N-terminal of $X_1$-arginine-threonine-proline-$X_2$-serine-threonine-tyrosine-arginine-leucine- (wherein "$X_1$" means valine or methionine and "$X_2$" means alanine or valine).

Experiment 14 (2)
Internal Partial Amino Acid Sequence

A part of a purified enzyme preparation derived from Rhizobium sp. M-11, obtained by the method in Experiment 2, and a part of a purified enzyme preparation derived from Arthrobacter sp. Q36, obtained by the method in Experiment 10, were dialyzed against 10 mM Tris-HCl buffer (pH 9.0), and the resultants were respectively diluted with a fresh preparation of the same buffer to give about one mg/ml. To one ml aliquots of the resultant solutions were added 10 μg "Lysyl Endopeptidase" commercialized by Wako Pure Chemical Industries, Ltd., Tokyo, Japan, and allowed to react at 30° C. for 22 hours to form peptides. The resultant mixtures were subjected to reverse phase high-performance liquid chromatography (reverse phase HPLC) to separate the peptides. The apparatus and conditions used to separate the peptides of the enzyme preparation from Rhizobium sp. M-11 on the reverse phase HPLC were "CAPCELL PAK C18 column", a diameter of 4.6 mm and a length of 250 mm, a product of Shiseido Co., Ltd., Tokyo, Japan; a flow rate, 0.6 ml/min; a temperature, an ambient temperature; an elution time, 60 min; and a gradient, a liner gradient of a solution containing 0.1 v/v % trifluoro acetate and acetonitrile ranging from 16–48 v/v %. The apparatus and conditions used to separate the peptides of the enzyme preparation from Arthrobacter sp. Q36 on reverse phase HPLC were "μ-Bondapak C18 column" having a diameter of 2.1 mm and a length of 150 mm, a product of Waters Chromatography Div., MILLIPORE Corp., Milford, USA; a flow rate, 0.9 ml/min; a temperature, an ambient temperature; an elution time, 60 min; and a gradient, a liner gradient of a solution containing 0.1 v/v % trifluoro acetate and acetonitrile ranging from 30–55 v/v %. The peptides eluted from the columns were detected by monitoring an absorbency at a wavelength of 210 nm. From the enzyme preparation of Rhizoblum sp. M-11 three peptides named as R37, R40 and R42 having the respective retention times of about 37, 40 and 42, and from the enzyme preparation of Arthrobacter sp. Q36 three peptides named as A17, A22 and A40 having the respective retention times of about 17, 22 and 40 were recovered after separation of concomitant peptides, followed by drying the resultant peptides in vacuo and dissolving them in 200 μl aliquot solutions with different concentrations of 0.1–50% acetonitrile. Each peptide specimen thus obtained was subjected to a protein sequencer to analyze its amino acid sequence up to 10 amino acid residues. The analyzed internal partial amino acid sequences were as shown in Table 12.

TABLE 12

| Origin | Peptide | Internal partial amino acid sequence |
|---|---|---|
| Rhizobium sp. M-11 | R37 | glycine-valine-glutamic acid-Aspartic acid-threonine-alanine-phenylalanine-phenylalanine-arginine-tyrosine- (SEQ. ID NO: 3) |
| | R40 | leucine-valine-glutamine-leucine-threonine-methionine-proline-glycine-valine-proline- (SEQ. ID NO: 4) |
| | R42 | glutamic acid-glycine-arginine-glycine-serine-proline-tyrosine-alanine-valine-alanine- (SEQ. ID NO: 5) |
| | A17 | glycine-valine-glutamic acid-aspartic acid-threonine-alanine-phenylalanine-phenylalanine-arginine-tyrosine- (SEQ. ID NO: 6) |
| Arthrobacter sp. Q36 | A22 | leucine-valine-glutamine-leucine-threonine-methionine-proline-glycine-valine-proline- (SEQ. ID NO: 7) |
| | A40 | glutamic acid-glycine-arginine-glutamine-serine-arginine-tyrosine-alanine-glutamic acid alanine- (SEQ. ID NO: 8) |

As evident from Table 12, the partial amino acid sequence of peptide R37 of the enzyme preparation from Rhizobium sp. M-11 completely coincided with that of peptide R40, while that of peptide R40 completely coincided with that of peptide A22. As regards peptides R42 and A40, they have 7 common amino acid residues among the analyzed 10 amino acid residues; i.e. peptides R42 and A40 have a common partial amino acid sequence of glutamic acid-glycine-arginine-$X_3$-serine-$X_4$-tyrosine-alanine-$X_5$-alanine- (wherein "$X_3$" means glycine or glutamine; "$X_4$", proline or arginine; and "$X_5$", valine or glutamic acid).

The following Examples A illustrate the preparation of the present non-reducing saccharides, relatively-low reducing saccharides containing them, and trehalose; and Examples B illustrate compositions containing one or more of these saccharides and trehalose.

EXAMPLE A-1

A seed culture of Rhizobium sp. M-11 (FERM BP-4130) was inoculated in a nutrient culture medium and incubated by a fermentor for about 36 hours in accordance with the method in Experiment 1. After completion of the incubation, the resultant culture was filtered to remove cells with an SF-membrane to obtain an about 18 L filtrate which was then concentrated with a UF-membrane to obtain about one L of a concentrated solution containing 17.7 units/ml of the present non-reducing saccharide-forming enzyme.

Six % suspension of potato starch, d.s.b., was gelatinized by heating, adjusted to pH 4.5 and 50° C., mixed with 2,500 units per g starch of isoamylase commercialized by Hayashibara Biochemical Laboratories Inc., Okayama, Japan, and subjected to an enzymatic reaction for 20 hours. The resultant mixture was adjusted to pH 6.0, autoclaved at 120° C. for 10 min, cooled to 45° C., admixed with 150 units per g starch of "Termamyl 60L", α-amylase commercialized by Novo Industri A/S, Copenhagen, Denmark, and subjected to an enzymatic reaction for 24 hours.

The reaction mixture was autoclaved at 120° C. for 20 min, cooled to 45° C., admixed with one unit per g starch of the above non-reducing saccharide-forming enzyme, and subjected to an enzymatic reaction for 96 hours. The resultant mixture was kept at 95° C. for 10 min, cooled and filtered. The resultant filtrate was in the usual manner decolored with an activated charcoal, and purified by desalting it with ion-exchange resins in H- and OH-form. The resultant solution was concentrated into a 70% syrup in a yield of about 91%, d.s.b.

The product exhibits a DE 18.8, and contains 8.3% P I, 5.5% P II, 37.7% P III, 1.4% P IV and 1.3% P V, d.s.b. The product has a mild and high-quality sweetness, as well as an adequate viscosity and moisture-retaining ability, and these render it arbitrary useful in food products, cosmetics and pharmaceuticals as a sweetener, taste-improving agent, quality-improving agent, stabilizer and filler.

EXAMPLE A-2

A saccharide solution as a feed solution, obtained by the method in Example A-1, was fractionated by using a column packed with "XT-1016 (Na$^+$-form, polymerization degree of 4%)", an alkaline metal strongly-acidic cation exchange resin commercialized by Tokyo organic Chemical Industries Ltd., Tokyo, Japan. The procedure was as follows: The resin was packed in 4 jacketed-stainless steel columns having an inner diameter of 5.4 cm, and the columns were cascaded in series to give a total gel-bed depth of 20 m. The columns were heated to give an inner column temperature of 55° C., and fed with 5 v/v % of the saccharide solution while keeping at the temperature, and the saccharide solution was fractionated by feeding to the columns 55° C. hot water to remove fractions rich in glucose and maltose, followed by recovering fractions rich in non-reducing saccharides. The fractions rich in non-reducing saccharides were pooled, purified, concentrated, dried in vacuo, and pulverized to obtain a powdery product containing non-reducing saccharides in a yield of about 61%, d.s.b.

The product exhibits a DE 5.7 and contains 9.3% P I, 7.4% P II, 55.5% P III, 2.1% P IV and 1.9% P V, d.s.b. Similarly as the product in Example A-1, the product has a mild and high-quality sweetness, as well as an adequate viscosity and moisture-retaining ability, and these render it arbitrarily useful in food products, cosmetics and pharmaceuticals as a sweetener, taste-improving agent, quality-improving agent, stabilizer and filler.

EXAMPLE A-3

Thirty-three % suspension of corn starch, d.s.b., was mixed with calcium carbonate to give the final concentration of 0.1%, d.s.b., and the resultant mixture was adjusted to pH 6.5, admixed with 0.2%, d.s.b., per g starch of "Termamyl 60 L", α-amylase commercialized by Novo Industri A/S Copenhagen Denmark, and subjected to an enzymatic reaction at 95° C. for 15 min. The reaction mixture was autoclaved at 120° C. for 10 min, cooled to 55° C., admixed with 5 units per g starch of maltotetraose-forming amylase commercialized by Hayashibara Biochemical Laboratories Inc., Okayama, Japan, and subjected to an enzymatic reaction for 6 hours. The resultant mixture was admixed with 30 units per g starch of "α-amylase 2A", α-amylase commercialized by Ueda Chemical Co., Ltd., Osaka, Japan, and subjected to an enzymatic reaction at 65° C. for 4 hours. The reaction mixture was autoclaved at 120° C. for 10 min, cooled to 45° C., admixed with 2 units per g starch of a non-reducing saccharide-forming enzyme obtained by the method in Example A-1, and subjected to an enzymatic reaction for 64 hours. The resultant mixture was kept at 95° C. for 10 min, cooled and filtered to obtain a filtrate which was then decolored with an activated charcoal in the usual manner, and purified by desalting it with ion-exchange resins in H- and OH-form, followed by concentrating the resultant solution to obtain a 70% syrup in a yield of about 90%, d.s.b.

The product exhibits a DE 10.5 and contains 3.7% P I, 43.7% P II, 1.2% P III, 1.1% P IV and 0.6% P V, d.s.b. The product has a mild and high-quality sweetness, as well as an adequate viscosity and moisture-retaining ability, and these render it arbitrary useful in food products, cosmetics and pharmaceuticals as a sweetener, taste-improving agent, quality-improving agent, stabilizer and filler.

EXAMPLE A-4

A saccharide solution as a feed solution, obtained by the method in Example A-3, was column chromatographed in accordance with the method in Example A-2 except that "50W-X4 (Mg$^{++}$-form)", a strongly-acidic cation exchange resin commercialized by Dow Chemical Co., Midland, Mich., USA, was used as a resin for fractionation in order to increase the content of non-reducing saccharide P II (DP 4) and to obtain a non-reducing saccharide P II-rich fraction. The fraction was purified, concentrated and spray dried to obtain a powdery product rich in non-reducing saccharides in a yield of about 40%, d.s.b.

The product contains 8.5% P I, 68.0% P II and 1.4% P III, d.s.b., as a non-reducing saccharide, and exhibits a DE 3.5 and a substantially non or low reducing power. Similarly as the product in Example A-3, the product has a mild and high-quality sweetness, as well as an adequate viscosity and moisture-retaining ability, and these render it arbitrarily useful in food products, cosmetics and pharmaceuticals as a sweetener, taste-improving agent, quality-improving agent, stabilizer and filler.

EXAMPLE A-5

To 20% aqueous solution of maltopentaose, commercialized by Hayashibara Biochemical Laboratories Inc., Okayama, Japan, was added 1.0 unit per g maltopentaose of a non-reducing saccharide-forming enzyme prepared by the method in Example A-1, and subjected to an enzymatic reaction at 45° C. for 48 hours. The enzymatic reaction resulted in a conversion of about 93%, d.s.b., maltopentaose into non-reducing saccharide P III. The reaction mixture was kept at 95° C. for 10 min, cooled and filtered to obtain a filtrate which was then in the usual manner decolored with an activated charcoal, desalted with ion-exchange resins in H- and OH-form, and concentrated. In order to increase the content of non-reducing saccharide P III (DP 5), the resultant concentrate was similarly as in Example A-2 column chromatographed by using an alkaline metal strongly-acidic cation exchange resin to obtain a P III-rich fraction. The fraction was purified, concentrated and spray dried to obtain a powdery product containing high-purity non-reducing saccharides in a yield of about 55%, d.s.b.

The product contained 99.0% P III as a non-reducing saccharide, d.s.b., and exhibited a DE of lower than about 0.2, the level of which is extremely low. The product has a slight sweetness and can be arbitrary used in food products, cosmetics and pharmaceuticals as a sweetener, taste-improving agent, quality-improving agent and stabilizer.

EXAMPLE A-6

Forty parts by weight of "PINE-DEX #4", a partial starch hydrolysate commercialized by Matsutani Chemical Ind., Tokyo, Japan, was dissolved in 60 parts by weight of water, and the resultant solution was heated to 45° C., adjusted to pH 6.5, mixed with one unit per g partial starch hydrolysate of a non-reducing saccharide-forming enzyme prepared by the method in Example A-1, and subjected to an enzymatic reaction for 96 hours while keeping at the temperature and pH. Thereafter, the reaction mixture was heated at 100° C. for 10 min to inactivate the remaining enzyme, diluted to give a concentration of about 20%, d.s.b., admixed with 10 units per g partial starch hydrolysate of "GLUCOZYME", glucoamylase commercialized by Nagase Biochemicals, Ltd., Kyoto, Japan, and subjected to an enzymatic reaction for 40 hours, followed by heating the resultant mixture to inactivate the remaining enzyme. The mixture thus obtained was in the usual manner decolored with an activated charcoal, desalted with an ion-exchange resin, and concentrated to give a concentration of about 60%, d.s.b. The saccharide solution thus obtained contained 29.5% trehalose, d.s.b. The saccharide solution was column chromatographed in accordance with the method in Example A-2 except that "CG 6000 (Na$^+$-form)", a strongly-acidic cation exchange resin commercialized by Japan Organo Co., Ltd., Tokyo, Japan, was used as a resin for fractionation, followed by recovering a trehalose-rich fraction. The fraction contained about 90% trehalose, d.s.b. The fraction was concentrated into an about 75% solution which was then placed in a crystallizer, admixed with about 2%, d.s.b., hydrous crystalline trehalose as a seed crystal and gradually cooled to obtain a massecuite with a degree of crystallization of about 45%. The massecuite was sprayed from a nozzle equipped on the top of a spraying tower at a pressure of 150 kg/cm$^2$. In the spraying step, the massecuite was simultaneously ventilated with 85° C. hot air sent from the top of the spraying tower, and the resultant crystalline powder was collected on a metal wire netting conveyer provided on the basement of the spraying tower, and gradually moved out of the tower while a stream of 40° C. air was passing upwards through the metal wire netting. The resultant crystalline powder was injected in an ageing tower and aged for 10 hours to complete the crystallization and drying, followed by recovering a powdery hydrous crystalline trehalose.

The product exhibits no substantial hygroscopicity and has a satisfiable handleability, and these render it arbitrary useful in food products, cosmetics and pharmaceuticals as a sweetener, taste-improving agent, quality-improving agent, stabilizer and filler.

EXAMPLE A-7

One part by weight of potato starch was admixed by stirring with 6 parts by weight of water containing 0.01% per g starch of "NEO-SPITASE", α-amylase commercialized by Nagase Biochemicals, Ltd., Kyoto, Japan, and the resultant suspension was adjusted to pH 6.0, heated to 85–90° C., and simultaneously gelatinized and liquefied at the temperature. Thereafter, the resultant was immediately heated to 120° C. for 5 min to keep the DE (dextrose equivalent) below 1.0, rapidly cooled to 55° C., adjusted to pH 7.0, admixed with 150 units per g starch of "PULLULANASE (EC 3.2.1.41)", an enzyme specimen commercialized by Hayashibara Biochemical Laboratories, Inc., Okayama, Japan, and 8 units per g starch of a maltotetraose forming enzyme described in Example A-3, and subjected to an enzymatic reaction at pH 7.0 and 50° C. for 36 hours.

The reaction mixture was autoclaved at 120° C. for 10 min, cooled to 45° C., admixed with 2 units per g starch of a non-reducing saccharide-forming enzyme derived from *Brevibacterium helovolum* ATCC 11822 prepared by the method in Experiment 13, and subjected to an enzymatic reaction for 64 hours. The reaction mixture was heated at 95° C. for 10 min, cooled and filtered. The resultant filtrate was decolorized in a conventional manner with an activated charcoal, desalted and purified with ion-exchange resins of H- and OH-form. The resultant solution was concentrated and spray dried to obtain a powdery non-reducing saccharides in a yield of about 90%, d.s.b.

The product exhibits a DE 11.2, contains 2.9% P I, 61.5% P II and 0.8% P III, d.s.b., and has a mild and high-quality sweetness, as well as a satisfactory viscosity and moisture-retaining ability, and these render it arbitrarily useful in compositions such as food products, cosmetics and pharmaceuticals as a sweetener, taste-improving agent, quality-improving agent and stabilizer.

EXAMPLE A-8

A seed culture of a microorganism of Arthrobacter sp. Q36 (FERM BP-4316) was inoculated in a nutrient culture medium and cultured with a fermentor for about 72 hours in accordance with the method in Experiment 9. The resultant culture was centrifuged to remove cells, and the resultant supernatant was concentrated by about 10 times with a UF-membrane to obtain an enzyme solution containing about 15.2 units/ml of the present non-reducing saccharide-forming enzyme.

In accordance with the method in Example A-3, 30% suspension of corn starch was subjected to the action of an α-amylase specimen commercialized by Novo Industri A/S, Copenhagen, Denmark; a maltotetraose forming amylase specimen commercialized by Hayashibara Biochemical Laboratories, Inc., Okayama, Japan; and an α-amylase specimen commercialized by Ueda Chemical Co., Ltd., Osaka, Japan. The resultant mixture was autoclaved at 120° C., cooled to 45° C., admixed with 2 units per g starch of a non-reducing saccharide-forming enzyme prepared by the above-mentioned method, and subjected to an enzymatic reaction for 64 hours. The reaction mixture was heated at 100° C. for 10 min to inactivate the remaining enzyme. In accordance with the method in Example A-6, the resultant solution was subjected to the action of glucoamylase commercialized by Nagase Biochemicals, Ltd., Kyoto, Japan, decolored, desalted and concentrated into an about 60% solution. The saccharide solution thus obtained contained about 25% trehalose, d.s.b. The saccharide solution was fractionated on column chromatography using a strongly-acidic cation-exchange resin to obtain fractions rich in trehalose. The fractions were pooled, placed in a vessel and boiled down under a reduced pressure into a syrup with a moisture content of about 4.0%. The syrup was placed in a crystallizer and admixed with one % of anhydrous crystalline trehalose, as a seed crystal, with respect to the syrup, d.s.b., followed by crystallizing anhydrous crystalline trehalose at 95° C. for 5 min while stirring. The resultant was transferred to an aluminum container and aged at 100° C. for 6 hours to form a block. The resultant block was pulverized by a cutting machine and subjected to a fluidized-bed drying to obtain a powdery anhydrous crystalline trehalose with a moisture content of about 0.3%.

The product can be arbitrarily used in hydrous matters such as food products, cosmetics and pharmaceuticals, and their materials and intermediates as a desiccant, as well as a white powdery sweetener with a high-quality and mild sweetness.

EXAMPLE B-1

Sweetener

To one part by weight of a powdery product rich in non-reducing saccharides, obtained by the method of Example A-4, was homogeneously added 0.01 part by weight of "αG Sweet", α-glycosyl stevioside commercialized by Toyo Sugar Refining Co., Ltd., Tokyo, Japan, and 0.01 part by weight of L-aspartyl-L-phenylalanine methylester commercialized by Ajinomoto Co., Ltd., and the mixture was fed to a granulator to obtain a granular sweetener. The product has a satisfactory sweetness and a 2-fold higher sweetening power sucrose, and the caloric value is about ½ of that of sucrose.

The product having a satisfiable stability neither affects nor decomposes other sweeteners with a relatively-high sweetness when mixed with them, and because of this it can be suitably used as a low-caloric sweetener for low-caloric food products for fat persons and diabetics who are restricted to a reduced calorie intake.

The product forms minimal amount of acid and insoluble glucans when dental carries-inducing microorganisms act on it, and this renders it useful for sweetening food products directed to the prevention of dental carries.

EXAMPLE B-2

Hard Candy

One hundred parts by weight of 55% sucrose solution was mixed with 30 parts by weight of a syrup containing non-reducing saccharides, obtained by the method in Example A-3, and the resultant mixture was concentrated by heating in vacuo until the moisture content was lowered to below 2%. The concentrated solution was admixed with one part by weight of citric acid and adequate amounts of a lemon flavor and a coloring agent, and the resultant mixture was formed in the usual manner to obtain the desired product.

The product is a high-quality hard candy having a satisfactory taste and biting property, as well as having no danger of changing the form and causing crystallization of sucrose.

EXAMPLE B-3

Chewing Gum

Three parts by weight of gum base was melted by heating until it softened, and the resultant was mixed with 4 parts by weight of sucrose and 3 parts by weight of a hydrous crystalline trehalose powder obtained by the method in Example A-6, and further mixed with adequate amounts of a flavor and a coloring agent. The resultant mixture was kneaded by a roll in the usual manner, formed and packed to obtain the desired product.

The product is a chewing gum having a satisfiable texture and taste.

EXAMPLE B-4

Sweetened Condensed Milk

Three parts by weight of a syrup containing non-reducing saccharides obtained by the method of Example A-1 and one part by weight of sucrose were dissolved in 100 parts by weight of fresh milk, and the resultant solution was sterilized by heating with a plate heater, and condensed into a 70% solution, followed by aseptically canning the resultant into the desired product.

The product with a mild sweetness and a satisfactory taste can be arbitrarily used as a seasoning for baby foods, fruit, coffee, cocoa and tea.

EXAMPLE B-5

Beverage Containing Lactic Acid Bacteria

One hundred and seventy-five parts by weight of defatted milk, 80 parts by weight of a high non-reducing saccharide content powder prepared by the method of Example A-2, and 50 parts by weight of a high lactosucrose content powder disclosed in Japanese Patent Laid-Open No.281, 795/92 were dissolved in 1,200 parts by weight of water, and the resultant solution was sterilized by heating at 65° C. for 30 min, cooled to 40° C., admixed in the usual manner with 30 parts by weight of lactic acid bacteria as a starter, and incubated at 37° C. for 8 hours to obtain a beverage containing lactic acid bacteria.

The product is a beverage containing lactic acid bacteria with a satisfiable taste and flavor. The product containing oligosaccharides retains lactic acid bacteria in a stable state and promotes the growth of bifid bacteria.

EXAMPLE B-6

Powdered Juice

Thirty-three parts by weight of powdered orange juice prepared by spray drying was mixed to homogeneity under stirring conditions with 50 parts by weight of a powder rich in non-reducing saccharides obtained by the method of Example A-2, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan, and an adequate amount of a powdered flavor. The resultant mixture was pulverized, fed to a fluidized-bed granulator and granulated for 30 min by spraying it with a syrup containing non-reducing saccharides as a binder obtained by the method in Example 1 while sending to the contents 40° C. air. The granules thus obtained were weighed and packaged to obtain the desired product.

The product contains 30% orange juice, d.s.b. The product was stable for a relatively-long period of time without giving an unsatisfactory taste and smell.

EXAMPLE B-7

Custard Cream

One hundred parts by weight of corn starch, 100 parts by weight of a syrup containing non-reducing saccharides obtained by the method in Example A-3, 80 parts by weight of maltose, 20 parts by weight of sucrose, and one part by weight of salt were mixed to homogeneity. The resultant mixture was admixed with 280 parts by weight of egg, and gradually added with 1,000 parts by weight of boiling milk. The mixture thus obtained was continued stirring while heating, and the heating was stopped when the corn starch in the mixture was completely gelatinized to render the contents semitransparent, followed by cooling the resultant and adding thereto an adequate amount of a vanilla flavor. The resultant mixture was weighed, injected and packaged to obtain the desired product.

The product has a smooth surface and gloss, as well as a mild taste and sweetness.

EXAMPLE B-8

An (beans paste)

Ten parts by weight of adzuki beans as a material was boiled by the addition of water in the usual manner, followed by removing the astringency and harshness of the beans, as well as water-soluble impurities, to obtain about 21 kg "adzuki-tsubu-an". To the resultant was added 14 parts by weight of sucrose, 5 parts by weight of a syrup containing non-reducing saccharides obtained by the method of Example A-3, and 4 parts by weight of water, and the resultant mixture was boiled, mixed with a small amount of salad oil, and carefully kneaded up so as not to paste the beans. Thus, the desired product was obtained in a yield of about 35 kg.

The product free from discoloration induced by boiling and has a satisfactory taste and flavor. These properties render it useful as a material an for bean-jam buns, buns with bean-jam filling, dumplings, bean-jam-filled wafers, sherbets and ice creams.

EXAMPLE B-9

Bread

One hundred parts by weight of wheat powder, 2 parts by weight of yeast, 5 parts by weight of sugar, one part by weight of a powder containing non-reducing saccharides obtained by the method of Example A-7, 0.1 part by weight of inorganic yeast food were kneaded with water in the usual manner to effect fermentation at 26° C. for 2 hours , and further aged for 30 min, followed by baking up the resultant.

The product is a high-quality bread having a satisfactory hue and volume, as well as a satisfiable elasticity and mild sweetness.

EXAMPLE B-10

Ham

To one thousand parts by weight of ham meat slices was added and ground to homogeneity 15 parts by weight of salt and 3 parts by weight of potassium nitrate, and the resultant slices were piled up and allowed to stand overnight in a cold-storage room. Thereafter, the resultant slices were first soaked for 7 days in a cold-storage room in a salt solution consisting of 500 parts by weight of water, 100 parts by weight of salt, 3 parts by weight potassium nitrate, 40 parts by weight of a powder containing non-reducing saccharides prepared by the method of Example A-7, and an adequate amount of a peppermint, then washed with cold water in the usual manner, tied up, smoked, cooked, cooled and packaged to obtain the desired product.

The product is a high-quality ham having a satisfactory hue, taste and flavor.

EXAMPLE B-11

Powdery Peptide

Forty % "Hinute S", a peptide solution of edible soy beans commercialized by Fuji Oil Co., Ltd., Tokyo, Japan, was mixed with 2 parts by weight of a powder containing hydrous crystalline trehalose prepared by the method of Example A-6, and the resultant mixture was placed in a plastic vessel, dried in vacuo at 50° C., and pulverized to obtain a powdery peptide. The product having a satisfactory taste and flavor can be arbitrarily used as a material for confectioneries such as premixes, sherbets and ice creams, as well as baby foods and therapeutic nutrition in the form of oral and intubation feedings.

EXAMPLE B-12

Powdery Egg Yolk

Egg yolks prepared from fresh eggs were sterilized at 60–64° C. by a plate heater, and the resultant liquid was mixed with 4 parts by weight of a powdery anhydrous crystalline trehalose prepared by the method of Example A-8 with respect to one part by weight of the liquid. The resultant mixture was transferred to a vessel, allowed to stand overnight to form a block while the anhydrous crystalline trehalose was permitted to hydrate hydrous crystalline trehalose. The block thus obtained was pulverized by a cutting machine to obtain a powdery egg yolk.

The product can be arbitrarily used as a material for confectioneries for premixes, sherbets, ice creams and emulsifiers, as well as baby foods and therapeutic nutrition in the form of oral and intubation feedings. The product can be also used as a skin refiner and hair restorer.

EXAMPLE B-13

Cosmetic Cream

Two parts by weight of polyoxyethylene glycol monostearate, 5 parts by weight of glyceryl monostearate, self-emulsifying, 2 parts by weight of a powder rich in non-reducing saccharides obtained by the method of Example A-2, one part by weight of α-glycosyl rutin, one part by weight of liquid petrolatum, 10 parts by weight of glyceryl tri-2-ethylhexanoate, and an adequate amount of an antiseptic were dissolved by heating in coventional manner. The resultant solution was admixed with 2 parts by weight of L-lactic acid, 5 parts by weight of 1,3-butylene glycol and 66 parts by weight of refined water, and the resultant mixture was emulsified by a homogenizer and admixed with an adequate amount of a flavor while stirring to obtain a cosmetic cream.

The product exhibits an antioxidant activity and has a relatively-high stability, and these render it arbitrarily useful as a high-quality sunscreen, skin-refining agent and skin-whitening agent.

EXAMPLE B-14

Solid Pharmaceutical

To a column of an immobilized anti-human interferon-α antibody was fed in conventional manner a natural human interferon-α preparation, commercialized by Cosmo Bio, Tokyo, Japan, to adsorb the interferon-α, and fed with a buffer containing calf serum albumin as a stabilizer, followed by removing an excessive amount of the albumin. Thereafter, the interferon-α was eluted with a physiological saline containing 5% of a high-purity non-reducing saccharides, d.s.b., obtained by the method in Example A-5, while varying the pH of the physiological saline.

The resultant eluate was membrane filtered, and the filtrate was dehydrated by about 20-fold volumes of "FINETOSE®", an anhydrous crystalline maltose powder commercialized by Hayashibara Shoji Inc., Okayama, Japan, followed by pulverizing the resultant dehydrated product, and tabletting the resultant by a tabletting machine into tablets containing about 150 units of the natural human interferon-α per one tablet, 200 mg weight.

The product can be orally administered as a sublingual tablet to patients at a dose of 1–10 tablets/adult/day, and arbitrarily used to treat viral diseases, allergys, rheumatisms, diabetes and malignant tumors. More particularly, the product can be suitably used as a therapeutic agent for AIDS and hepatitis, the number of patients of which has increased remarkably. The present non-reducing saccharides and anhydrous crystalline maltose incorporated in the product act as a stabilizer for the natural human interferon-α, so that the activity is well retained for a relatively-long period of time even at ambient temperature.

EXAMPLE B-15

Sugar Coated Tablet

A crude tablet as a core, 150 mg weight, was coated with a solution consisting of 40 parts by weight of a powdery hydrous crystalline trehalose obtained by the method of Example A-6, 2 parts by weight of pullulan having an average molecular weight of 200,000, 30 parts by weight of water, 25 parts by weight of talc, and 3 parts by weight of titanium oxide until the total weight reached to about 230 mg, and the resultant was further coated with a solution consisting of 65 parts by weight of a fresh preparation of the same powdery hydrous crystalline trehalose, one part by weight of pullulan, and 34 parts by weight of water, and glossed with a liquid wax to obtain a sugar coated tablet having a satisfiable gloss and appearance.

The product has a relatively-high shock tolerance and retains its high quality for a relatively-long period of time.

As evident from above, the present novel non-reducing saccharide-forming enzyme converts reducing partial starch hydrolysates into non-reducing saccharides in a satisfactorily-high yield under a relatively-mild enzymatic reaction condition without changing the degrees of glucose polymerization of the reducing partial starch hydrolysates. The non-reducing saccharides, which can be readily separated and purified, and relatively-low reducing saccharides containing them, as well as trehalose prepared from these saccharides, have a satisfactory stability, quality and mild sweetness. These products are assimilated and utilized as an energy source by the body when orally administered. These non-reducing saccharides, relatively-low reducing saccharides containing them, and trehalose prepared from these saccharides can be arbitrarily used in compositions such as food products, cosmetics and pharmaceuticals as a sweetener, taste-improving agent, quality-improving agent, stabilizer and filler.

Thus, the present invention provides a novel technique to prepare in an industrial-scale and at a relatively-low cost non-reducing saccharides, which could not have been readily obtained in spite of their great demands, by using reducing partial starch hydrolysates prepared from starch as a cheap and abundant source, as well as to prepare relatively-low reducing saccharides containing the non-reducing saccharides, and trehalose prepared from these saccharides. The present invention has a great influence on the fields such as starch-, enzyme- and biochemical-sciences; and other industrial fields, especially, food-, cosmetic- and pharmaceutical-industries, as well as forestry, fisheries, and agricultural-, livestock- and chemical-industries. Thus, the influence of the present invention on these fields is unfathomable.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for producing a non-reducing saccharide having a trehalose structure comprising:
   (a) contacting a solution containing a reducing partial starch hydrolysate with an enzyme which forms in the absence of trehalose saccharide having a trehalose structure when allowed to act on a reducing partial starch hydrolysate to form a non-reducing saccharide;
   (b) recovering said non-reducing saccharide together with or without the remaining reducing partial starch hydrolysates;
   wherein said reducing partial starch hydrolysate is one or more reducing partial starch hydrolysates having a degree of glucose polymerization of 3 or more.

2. The process of claim 1 wherein the trehalose structure in said non-reducing saccharide is located in its end unit.

3. The process of claim 2 wherein said non-reducing saccharide is an α-glucosyl trehalose shown by the formula:

$G_n$-T wherein the symbol "G" means glucose residue;
the symbol "n" means one or more integers; and the symbol "T" means α,α-trehalose residue.

4. A biologically pure culture of a microorganism which produces an enzyme that forms in the absence of trehalose a non-reducing saccharide having a trehalose structure when allowed to act on a reducing partial starch hydrolysate, and which is a microorganism selected from the group consisting of mutants Brevibacterium helovolum ATCC 11822, Flavobacterium aquatitle IFO 3722, Micrococcus luteus IFO 15321, Mycobacterium smegmatic ATCC 19420 and Terrabacter tumescens IFO 12960 said biologically pure culture containing said enzyme.

5. A process for producing a food product comprising:
   (a) contacting a solution containing a reducing partial starch hydrolysate with an enzyme which forms in the absence of trehalose a non-reducing saccharide having a trehalose structure when allowed to act on a reducing partial starch hydrolysate to form a non-reducing saccharide;
   (b) recovering said non-reducing saccharide together with or without the remaining reducing partial starch hydrolysate, wherein said reducing partial starch hydrolysate is one or more reducing partial starch hydrolysates having a degree of glucose polymerization of 3 or more; and
   (c) incorporating said non-reducing saccharide with or without the remaining reducing partial starch hydrolysate in step (b) into an edible material.

6. The process according to claim 5 wherein the trehalose structure in said non-reducing saccharide is located at the end unit thereof.

7. The process according to claim 5 wherein said non-reducing saccharide is an α-glycosyl trehalose of the formula:

$G_n$-T wherein G is a glucose residue;

n is at least one integer;

T is an α,α-trehalose residue.

8. A process for producing a cosmetic comprising:

(a) contacting a solution containing a reducing partial starch hydrolysate with an enzyme which forms in the absence of trehalose a non-reducing saccharide having a trehalose structure when allowed to act on a reducing partial starch hydrolysate to form a non-reducing saccharide;

(b) recovering said non-reducing saccharide together with or without the remaining reducing partial starch hydrolysate, wherein said reducing partial starch hydrolysate is one or more reducing partial starch hydrolysates having a degree of glucose polymerization of 3 or more; and (c) incorporating said non-reducing saccharide with or without the remaining reducing partial starch hydrolysate in step (b) into a cosmetic material.

9. The process according to claim 8 wherein the trehalose structure in said non-reducing saccharide is located at the end unit thereof.

10. The process according to claim 8 wherein said non-reducing saccharide is an α-glycosyl trehalose of the formula:

$G_n$-T wherein G is a glucose residue;

n is at least one integer;

T is an α,α-trehalose residue.

11. A process for producing a pharmaceutical comprising:

(a) contacting a solution containing a reducing partial starch hydrolysate with an enzyme which forms in the absence of trehalose a non-reducing saccharide having a trehalose structure when allowed to act on a reducing partial starch hydrolysate to form a non-reducing saccharide;

(b) recovering said non-reducing saccharide together with or without the remaining reducing partial starch hydrolysate, wherein said reducing partial starch hydrolysate is one or more reducing partial starch hydrolysates having a degree of glucose polymerization of 3 or more; and (c) incorporating said non-reducing saccharide with or without the remaining reducing partial starch hydrolysate in step (b) into a cosmetic material.

12. The process according to claim 11 wherein said non-reducing saccharide is an α-glycosyl trehalose of the formula:

$G_n$-T wherein G is a glucose residue;

n is at least one integer;

T is an α,α-trehalose residue.

13. The process according to claim 11 wherein the trehalose structure in said non-reducing saccharide is located at the end unit thereof.

* * * * *

UNITED STATES PATENT AND TRADEMARK OFFICE
CERTIFICATE OF CORRECTION

PATENT NO. : 5,922,580
DATED : July 13, 1999
INVENTOR(S) : Maruta et al.

It is certified that error appears in the above-identified patent and that said Letters Patent is hereby corrected as shown below:

Column 39,
Line 48, between "trehalose" and "saccharide" insert -- a --.
Line 60, delete "α-glucosyl" and insert therefor -- α-glycosyl --.

Signed and Sealed this

Twenty-third Day of March, 2004

JON W. DUDAS
*Acting Director of the United States Patent and Trademark Office*